United States Patent
Singh et al.

(10) Patent No.: US 8,277,843 B2
(45) Date of Patent: Oct. 2, 2012

(54) PROGRAMMABLE BUOYANT DELIVERY TECHNOLOGY

(75) Inventors: Amarjit Singh, Mumbai (IN); Sarabjit Singh, Mumbai (IN); Shivanand Puthli, Mumbai (IN); Rajendra Tandale, New Delhi (IN)

(73) Assignee: Panacea Biotec Limited, Maharashtra (IN)

( * ) Notice: Subject to any disclaimer, the term of this patent is extended or adjusted under 35 U.S.C. 154(b) by 553 days.

(21) Appl. No.: 12/439,775

(22) PCT Filed: Sep. 3, 2007

(86) PCT No.: PCT/IN2007/000392
§ 371 (c)(1),
(2), (4) Date: Mar. 3, 2009

(87) PCT Pub. No.: WO2008/062440
PCT Pub. Date: May 29, 2008

(65) Prior Publication Data
US 2010/0015224 A1    Jan. 21, 2010

(30) Foreign Application Priority Data
Sep. 4, 2006    (IN) .......................... 1411/MUM/2006

(51) Int. Cl.
*A61K 9/24*    (2006.01)
(52) U.S. Cl. ........................................ 424/472
(58) Field of Classification Search .................. None
See application file for complete search history.

(56) References Cited

U.S. PATENT DOCUMENTS

| | | | | |
|---|---|---|---|---|
| 4,127,622 A * | 11/1978 | Watanabe et al. | ............... | 264/13 |
| 5,314,696 A * | 5/1994 | Paulos | ........................... | 424/453 |
| 5,443,843 A * | 8/1995 | Curatolo et al. | .............. | 424/464 |
| 5,658,589 A * | 8/1997 | Parekh et al. | ................. | 424/463 |
| 5,895,663 A * | 4/1999 | Irwin et al. | .................... | 424/468 |
| 2003/0143257 A1 * | 7/2003 | Fleshner-Barak et al. | ..... | 424/426 |
| 2010/0040883 A1 * | 2/2010 | McCarthy et al. | ............ | 428/403 |

FOREIGN PATENT DOCUMENTS

| | | |
|---|---|---|
| EP | 1 574 534 | 9/2005 |
| JP | 3-101615 | 4/1991 |
| WO | 99/01112 | 1/1999 |
| WO | 01/58424 | 8/2001 |

OTHER PUBLICATIONS

"Sudafed®" product of McNeil-PPC Inc. website (http://www.sudafed.com/products), p. 1 (retrieved from online Sep. 8, 2011).*
"Motrin®" product of McNeil-PPC Inc. websites (http://www.motrin.com/), p. 1 (retrieved from online Sep. 8, 2011).*

(Continued)

*Primary Examiner* — Bethany Barham
(74) *Attorney, Agent, or Firm* — Ladas & Parry LLP

(57) ABSTRACT

The present invention is concerned with a system for spatially and temporally programmable delivery of an active agent. When administered orally, the System can be retained in the gastric region for a prolonged period of time. It comprises of a core (I), one or more layers (II, IV, V) coated over the core and a preformed hollow space (III). The invention also concerns with a process for preparation of the System and a method for treating/preventing diseases, by administering to a subject in need thereof, the System of the invention.

47 Claims, 6 Drawing Sheets

OTHER PUBLICATIONS

Senthil et al "Formulation and Evaluation of Tizanidine Hydrochloride microspheres by using 3^2Full Factorial Designs" International Research Journal of Pharmacy, 2011, 2 (9) p. 110-115.*

Xagoraraki et al "Effect of pH on degradation of acetaminophen and production of 1,4-benzoquinone in water chlorination" Journal of Water Supply: Research and Technology—AQUA, 57, 6, 2008, p. 381-390.*

New Zealand Data Sheet "Apo-oxybutynin" from Apotex NZ ltd online (www.medsafe.govt.nz/profs/datasheet/a/Apooxybutynintabsyrup.pdf) pp. 1-4.*

"pH Importance and What Happens to What You Eat?" from http://www.phcapsule.com/whtwye.htm retrieved online on Feb. 23, 2012, p. 1.*

New Zealand Data Sheet "Apo-oxybutynin" from Apotex NZ ltd online (www.medsafe.govt.nz/profs/datasheet/a/Apooxybutynintabsyrup.pdf) pp. 1-4; dated: Mar. 13, 2002.*

English abstract of JP 3-101615 dated Apr. 26, 1991.

* cited by examiner

PROGRAMMABLE BUOYANT DELIVERY TECHNOLOGY

FIELD OF THE INVENTION

The invention is in the field of pharmaceutical science. It relates to a system for spatially and temporally programmable delivery of an active agent. When administered orally, the system can be retained in the gastric region for a prolonged period of time.

BACKGROUND OF THE INVENTION

Gastric retention systems for delivery of active agents in the upper part of the gastrointestinal tract are well known. Some active agents show preferential solubility and/or absorption in the stomach or the proximal part of the gastrointestinal tract. In such cases, gastric retention systems can deliver active agents at their preferred site of absorption, thereby improving bioavailability and reducing wastage. Such systems also find application for delivery of actives which act locally in the gastric and proximal intestinal regions, such as antacids, anti-ulcer agents etc. Other applications include delivery of active agents which exhibit a narrow absorption window, which degrade in the colon and which are poorly soluble at an alkaline pH.

Various approaches have been used to formulate systems which exhibit a prolonged gastric retention. These approaches include utilization of mechanisms such as bioadhesion (Jackson et al, *Comparative scintigraphic assessment of the intragastric distribution and residence of cholestyramine, Carbopol 934P and sucralfate, Int J Pharm*, 212, 2001; U.S. Pat. No. 6,207,197; United States Patent Application No. 20050064027), swelling (Chavanpatil M et al, *Development of sustained release gastroretentive drug delivery system for ofloxacin: in vitro and in vivo evaluation, Int J Pharm*, 304(1-2), 2005), floatation (Arora S. et al, *Floating Drug delivery systems: A review, AAPS PharmSciTech* 6, (3), *Art.* 47, 2005), sedimentation, rafts and unfolding systems (Hampson F. et al, *Alginate rafts and their characterization, Int J. Pharm.* 294(1-2), 2005) and simultaneous administration of gastro active agents.

An approach for increasing the gastric residence time is to produce floating systems. These systems have a density less than the gastric fluids and hence they are buoyant, i.e. they tend to float in the stomach. Since the pylorus i.e. the exit to the intestines, is located in the lower part of the stomach, they are not discharged into the intestines for a long period of time.

A mechanism to produce floatation is to produce effervescent systems. (Dave et al, *Gastroretentive Drug Delivery System of Ranitidine Hydrochloride: Formulation and In Vitro Evaluation, AAPS PharmSciTech*, 5, 2, *Article* 34, 2004; Ichikawa M, et al, A new multiple unit oral floating dosage system. 1: *Preparation and in vitro evaluation of floating and sustained-release kinetics, J Pharm Sci*, 80, 1991; Ozdemir N et al, *Studies of floating dosage forms of furosemide: in vitro and in vivo evaluation of bilayer tablet formulation, Drug Dev Ind Pharm.* 26, 2000). These systems utilize gas-generating materials, such as carbonates. On reacting with the gastric acids, the materials generate carbon dioxide, which inflates the systems and allows them to float. Such systems are however highly dependant on gastric conditions, such as acidity, for successful functioning. An approach to make them independent of gastric acids is to incorporate pharmaceutically acceptable acidic substances, with basic substances into the formulations, and allowing them to react when the system comes in contact with a fluid, such as the gastric fluid. These systems, however, generally become moisture sensitive and present mechanical and chemical stability problems, making their manufacturing and packaging cumbersome.

Another approach is to incorporate a buoyant material into a system, which causes it to float. Hydrophobic materials, such as lipids, oils and waxes are used for these purposes. (Sriamornsak P. et al, *Morphology and Buoyancy of Oil-entrapped Calcium Pectinate Gel Beads, The AAPS Journal*, 6, 3, 2004; Shimpi S, et al, *Preparation and evaluation of diltiazem hydrochloride-Gelucire 43/01 floating granules prepared by melt granulation, AAPS PharmSciTech.* 5, *E*43, 2004).

Matrix type and bilayer systems are known which utilize swellable materials such as polymers, hydrocolloids etc. (U.S. Pat. No. 5,232,704). The swellable materials, such as alginate, polymers, gums swell on coming in contact with fluids, reduce the density of the system and causes it to float. The increase in size of the system may also present a mechanical barrier preventing exit through the pylorus. However, in practical use, these systems often exhibit inadequate performance, reproducibility issues or need elaborate processing requirements. Also, the functional materials used are often not biodegradable. As a result, a ghost of the system remains, which may pass through the intestines unchanged and cause unacceptable blockages.

Most of these above mechanisms require the presence of fluids to activate their floatation characteristics. They tend to be dependant on gastric conditions to function effectively. But gastrointestinal conditions are inherently highly variable. The conditions depend upon and vary with many physiological factors such as diet, fluid intake, age, gender, stress conditions and disease states. Hence, although successful in in-vitro conditions, many such systems fail to function effectively in the human physiology.

To overcome some of the above mentioned problems, dosage forms such as hollow or light microcapsules and beads have been formulated. (Kawashima et al, *Hollow microspheres for use as a floating controlled drug delivery system in the sto mach, J Pharm Sci*, 81, (2), 1992; Patel et al, *In vitro Evaluation and Optimization of Controlled Release Floating Drug Delivery System Of Metformin Hydrochloride, DARU*, 14, 2, 2006; Talukder R et al, *Gastroretentive Delivery Systems Hollow Beads, Drug Development and Industrial Pharmacy*, 30, 4, 2004; Streubel A et al, *Floating microparticles based on loss density foam powder, Int J Pharm*, 241, 2002; U.S. Pat. No. 6,207,197). Although these systems are less dependant on gastric conditions, they often utilize specialized and costly raw materials and involve elaborate complex; variable and time consuming processes, which are expensive and not too scale-up friendly.

Aerogels and foam materials have been used to produce floating systems. Due to entrapped air and gases in their hollow spaces, they are inherently less dense and hence float on the gastric fluids. U.S. Pat. No. 5,626,876 discloses floatable oral therapeutic systems which use microporous materials having a high void proportion for obtaining low specific gravity. The materials used are thermoplastic polymers, natural polymers and inorganic compounds such as glasses and ceramic materials. The invention relates to preparation of microporous materials by processes such as granulation, hot melting, compression or molding. U.S. Pat. No. 3,976,764 discloses solid therapeutic preparations floatable in the gastric juice wherein the active ingredient is impregnated into a body of empty globular shell or a small granular lump of a material having high buoyancy. The empty shells of the invention are gelatin capsules coated with active ingredients. The invention also discloses pop-corn or pop-rice type of materials coated with active ingredients. Use of microporous materials tends to increase the bulk of the systems. There is also less flexibility for designing the dosage form and incorporating active ingredients. Such systems may also be complex and less reproducible.

There is a need in the art to formulate a system which overcomes most of the above mentioned disadvantages, and is yet simple, safe, easy to manufacture and is functionally reproducible. Especially, there is a need for a system which does not depend on gastric conditions for it proper functioning.

OBJECTS OF THE PRESENT INVENTION

It is an object of the present invention to provide a system which meets most of the above mentioned needs.

It is an object of the present invention to provide a system which:

i. can be adapted to provide any desired type of delivery of an active agent,
ii. when given orally, can provide prolonged gastric retention and thereby a prolonged presence in the gastrointestinal tract,
iii. when given orally, is substantially independent of gastric conditions for its proper functioning,
iv. is easy to manufacture, amenable to large scale production, does not require sophisticated equipments and uses common raw materials which are biodegradable, non-toxic and biocompatible.

It is further an object of the present invention to provide a system which is versatile regarding the types of active ingredients which can be incorporated therein; the ingredients may be water soluble or insoluble, low dose or high dose.

SUMMARY OF THE INVENTION

The present invention is directed to such a system, which can provide for a delivery of an active agent, which is both spatially and temporally programmable. The system comprises of a core, one or more layers coated over the core and a preformed hollow space, wherein the active agent is present in the core or any of the layers of the system. The hollow space, which is preformed, i.e. formed during the manufacturing of the system, is present between two or more layers or between the core and one or more layers of the system.

When the system is administered orally, it can be retained in the gastric region for a prolonged period of time, from about 1 hour to about 18 hours.

In certain embodiments, the system comprises of a core, a polymeric layer, an active agent containing layer coated over the polymeric layer and a preformed hollow space.

In preferred embodiments, the system comprises of:
a core optionally comprising an active agent;
a first polymeric layer comprising a hydrophilic material;
a second polymeric layer comprising a polymer substantially insoluble in the gastric fluid;
an active agent containing layer coated over the second polymeric layer;
and a preformed hollow space substantially present between the first polymeric layer and the second polymeric layer.

In certain embodiments, the system comprises of a core, one or more polymeric layers coated over the core and a preformed hollow space, wherein the active agent is present in the core and wherein the active agent is delivered in the lower intestinal and/or the colonic region when the system is administered orally.

In certain alternative embodiments, the system comprises of:
a core comprising a hydrophilic material;
a polymeric layer comprising a polymer substantially insoluble in the gastric fluid;
an active agent containing layer;
and a preformed hollow space wherein the preformed hollow space is present substantially between the core and the polymeric layer.

In an embodiment, the present invention relates to a system retained in the gastric region for a prolonged period of time comprising a core, one or more layers coated over the core and a preformed hollow space. The active agent is present in the core or any of the layers of the system and the preformed hollow space is substantially present between two or more layers or between the core and one or more layers of the system The present invention is also directed to a process for manufacture of the system of the invention comprising the steps of manufacturing a core, or using a preformed core, optionally with an active agent;

optionally coating the core with a hydrophilic material to form the first polymeric layer;

further coating the system with a polymer substantially insoluble in the gastric fluid to form the second polymeric layer;

supplying energy and/or vacuum over a period ranging from about a few seconds to about 5 hours, causing the expansion of the second polymeric layer and generation of a hollow space; and optionally coating the above system with an active agent to form an active agent containing layer.

The process of the present invention is a process for manufacturing a system having a density lesser than gastrointestinal fluids comprising the step of formation of a hollow space within the system due to expansion of one or more of its compartments. The expansion is caused by generation of a positive or negative pressure within the system. Positive pressure is vapor pressure generated due to supply of energy, preferably heat. Negative pressure can be generated due to supply of vacuum. The expansion of the one or more compartments is preferably a plastic expansion, such that the hollow space is maintained in integrity after the removal of pressure.

The present invention also relates to a method for treating and/or preventing diseases, comprising the step of administering to a subject in need thereof the system of the invention, comprising the active agent in an effective amount.

DESCRIPTION OF THE INVENTION

Figure 1:
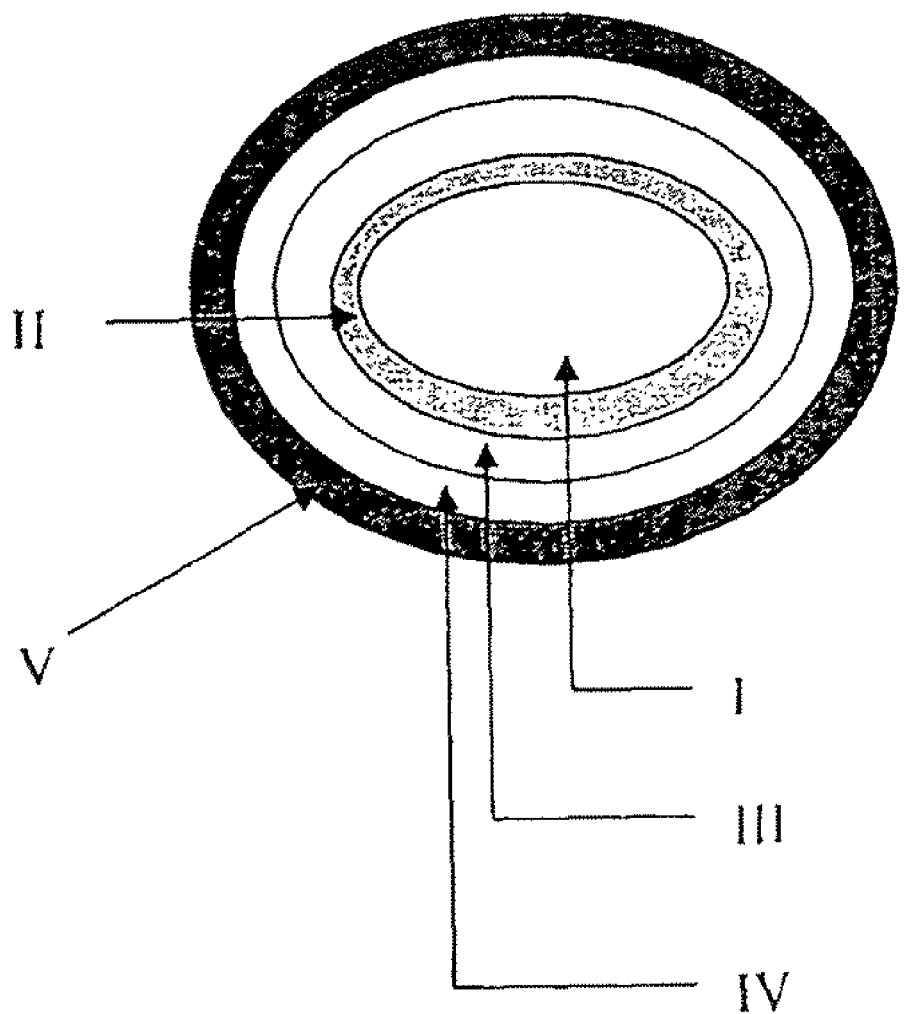
FIG. 1 shows an illustrative design and embodiment of the invention. It depicts the following compartments: Core (I), Optional first polymeric layer (II), Preformed hollow space (III), Second polymeric layer (IV), Active agent containing layer (V).

Before the composition and process of the present invention are disclosed and described, it is to be understood that this invention is not limited to the particular systems, process steps, and materials disclosed herein as modification to these may occur to a person skilled in the art. It is also to be understood that the terminology employed herein is used for the purpose of describing particular embodiments only and is not intended to be limiting since the scope of the present invention will be limited only by the appended claims and equivalents thereof.

It must be noted that as used in the specification and the appended claims, the singular forms 'a', 'an' and 'the' include plural references unless the context clearly indicates otherwise. Thus for example, use of the term 'an active agent' includes reference to one or more active agents.

By 'active agent' as used herein is meant an agent, active ingredient, substance or compound having beneficial physiologic, prophylactic, pharmacologic, diagnostic and/or therapeutic properties when administered to an animal, especially humans. The term 'active agent' also includes solvates, hydrates, active metabolites, prodrugs, derivatives, and all pharmaceutically acceptable complexes and salts thereof.

'Spatially and temporally programmable delivery of an active agent' as used herein indicates that the system of the invention can be adapted to deliver the active agent effectively from a specific region of the gastrointestinal tract (spatial control) and over a specific period of time (temporal control). The system can be adapted for both spatially and temporally programmable delivery at the same time or can be adapted for either spatial delivery or temporal delivery.

The preformed 'hollow space' in the system of the present invention is generated during the process of manufacturing the system. The space is maintained in integrity and is stable and may be filled by vapor or air or any gaseous substance or a partial vacuum. The space is formed by generation of a positive or negative pressure within the system and subsequent expansion of specific compartments of the system.

By 'buoyant' as used herein is meant that the system of the invention may have a density which is lesser than the density of the gastric fluid, causing it to float on the fluid.

By 'prolonged gastric retention' or 'gastric retention for a prolonged period of time' as used herein is meant retention in the stomach for a time period that lasts for several hours to about 24 hours, say from about one hour to about 24 hours, usually from about 1 hour to about 18 hours, more commonly up to about 3 to 8 hours.

By 'modified release' as used herein is meant release, which is not immediate release and is taken to encompass controlled release, sustained release, prolonged release, timed release, retarded release, extended release, pulsatile release and delayed release.

'System' as used herein includes a composition, formulation, device or an assembly which can be administered to a subject, preferably orally, and which can be utilized for the delivery of an active agent within the body of the subject.

The present invention relates to a system, which can provide for a delivery of an active agent, which is both spatially and temporally programmable and the process for its manufacture. The system comprises of a core, one or more layers coated over the core and a preformed hollow space, wherein the active agent is present in the core or any of the layers of the system. The hollow space, which is preformed, i.e. during the manufacturing of the system, is present between two or more layers or between the core and one or more layers of the system.

Preferably, the system is administered orally and it can be retained in the gastric region for a prolonged period of time, from about 1 hour to about 18 hours. The system may be in any form, such as tablets, capsules, beads or pellets.

The structure and function of the system shall be apparent from the following description of the invention and its embodiments. FIG. 1 shows an illustrative design and embodiment of the invention. Preferably, it comprises of the following compartments: a core (I), an optional first polymeric layer (II), a hollow space (III), a second polymeric layer (IV) and an active agent containing layer (V).

Each compartment generally present in the system is described in details as follows.

Core:

The innermost area of the system is the core (I). The core may be a compressed or molded system as in case of solid unit dosage forms (e.g. a tablet) or can be non-pareil seeds, preformed pellets or compressed systems as in case of multiparticulate dosage forms. In an embodiment, the core may be prepared as a multiparticulate system by granulation or by extrusion and spheronization. Alternatively, preformed cores such as non-pareil seeds may be used. In another embodiment, the cores may be prepared by compression or molding as a single tablet. Such formulations and processes for their preparation are well known in the art and are included herein by reference.

The core is comprised of one or more excipients normally encountered in the art such as fillers, diluents, binders, disintegrants, stabilizers, surfactants, wetting agents, buffering agents, preservatives, absorption enhancers, wicking agents, glidants, lubricants etc.

Diluents, also known as fillers, typically function as carriers and increase the bulk of the system so that a practical size is provided for manufacturing, such as compression of tablets and formation of beads or granules. Suitable diluents include, for example, lactose, sucrose, mannitol, sorbitol, microcrystalline cellulose, powdered cellulose, dry starch, hydrolysed starches, pregelatinized starch, dicalcium phosphate, calcium sulfate and titanium dioxide.

Binders are used to impart cohesive qualities to a system, to ensure its intactness. Suitable examples include starch, pregelatinized starch, polyvinylpyrrolidone, ethylcellulose, methylcellulose, microcrystalline cellulose, a derivatized cellulose, such as carboxymethyl cellulose, sodium carboxymethyl cellulose, hydroxyethyl cellulose, hydroxypropyl methylcellulose, and hydroxypropyl cellulose, polyethylene glycol, waxes, natural and synthetic gums such as acacia, tragacanth, sodium alginate and veegum.

Disintegrants are used to facilitate disintegration of the system after administration. Suitable examples include starch, sodium starch glycolate, carbopol, various celluloses, sodium carboxymethyl cellulose, clays, gums such as agar, arabic, guar, locust bean and crosslinked polymers such as crosslinked PVP and crosslinked carboxymethyl cellulose.

Lubricants prevent sticking and facilitate smooth manufacturing of a system. Suitable examples include magnesium stearate, stearic acid and its pharmaceutically acceptable alkali metal salts, calcium stearate, sodium stearate, Cab-O-Sil, Syloid, polyethylene glycol, magnesium lauryl sulfate, sodium stearyl fumarate, vegetable oil and talc.

In case of inclusion of active agents which exhibit low bioavailability, such as proteins, peptides and other macromolecules, absorption enhancers may be included in the core. These enhancers assist in increasing the absorption of active agent molecules through the gastrointestinal mucosa and improving their bioavailability. Absorption enhancers which may be used belong to categories such as cell envelope disordering compounds, solvents, steroidal detergents, bile salts, chelators, surfactants, non-surfactants, fatty acids etc. Examples include chelators such as EDTA, citric acid, sodium salicylate; surfactants such as sodium lauryl sulphate, benzalkonium chloride, polyoxyethylene, 23-lauryl ether; bile salts such as sodium deoxycholate, sodium glycocholate, sodium taurocholate; fatty acids such as oleic acid, capric acid, lauric acid; non-surfactants such as cyclic ureas, cyclodextrins; and others such as polysorbates, aprotinin, azone, alkyl glycosides, chitosan, menthol, dextran sulfate etc.

In an embodiment, when the first polymeric layer surrounding the core is absent, the core may additionally comprise of hydrophilic materials such as celluloses, alkylcelluloses, carboxyalkylcelluloses, natural, semisynthetic, or synthetic polysaccharides, acrylic acids and the salts thereof, polymethacrylic acids and the salts thereof, methacrylate copolymers, polyvinyl alcohol, vinyl polymers, polyvinylpyrrolidone, copolymers of polyvinylpyrrolidone with vinyl acetate, polyalkylene oxides and combinations thereof.

A complete list of such excipients described in detail can be found in the *Handbook of Pharmaceutical Excipients*, 3rd Edition, A. H. Kibbe, Editor, American Pharmaceutical Association, and Pharmaceutical Press (2000).

In certain preferred embodiments, the core comprises of about 10% to about 99.5% w/w diluent, about 0% to about 50% w/w binder and about 0.05% to about 10% w/w of lubricant. The core is manufactured by compression using compression equipments commonly known in the art. Tooling of any desired shape may be used for compression. However, preferred are shapes such as round, oval, capsule shaped, spherical, cylindrical, triangular, square, rectangular or polygonal.

The core can also optionally comprise of one or more active agents. If present, the active agent can be delivered when the system reaches the lower portion of the gastrointestinal tract, such as the lower intestinal and/or the colonic region. Alternatively, the active agent in the core can also be delivered in the gastric region, after a specific delay. The system may be programmed to release the active agent either all at once or in a modified release fashion. Methods to obtain such release profiles are well known in the art. For example, for immediate release, the core may comprise of disintegrants which assist in quick disintegration of the system and delivery of active agents. For modified release, use is made of rate controlling polymers or any other rate controlling excipients known for such purpose. Rate controlling polymers or excipients include, for example, various natural and synthetic polymers, gums of plant, animal, mineral or synthetic origin, substituted or unsubstituted hydrocarbons, such as fatty acids, fatty alcohols, glyceryl esters of fatty acids, mineral and vegetable oils and waxes.

The various natural and synthetic polymers include, for example, both hydrophilic and hydrophobic polymers known in the art.

Thus in an embodiment, the system of the invention comprises of an active agent and a rate controlling material in a matrix or a coating form.

The active agent can be incorporated into matrices of the core and then released by erosion of or diffusion through these matrices. Alternatively, the actives are layered onto tablets, multiparticulate beads or non-pareil seeds, using suitable binders and solvent systems. Methods for such loading and incorporation of active agents are well known in the art.

First Polymeric Layer:

Adjacent to the core is the optional First polymeric layer (II). The First polymeric layer substantially encapsulates the core. It comprises of one or more hydrophilic materials. The examples of such materials may be polymers, which are celluloses and alkylcelluloses, such as, methyl cellulose; hydroxyalkylcelluloses, for example, hydroxymethyl cellulose, hydroxyethyl cellulose, hydroxypropyl cellulose and hydroxybutyl cellulose; hydroxyalkyl alkylcelluloses, such as, hydroxyethyl methyl cellulose and hydroxypropyl methyl cellulose, carboxyalkylcelluloses, such as, carboxymethylcellulose; alkali metal salts of carboxyalkylcelluloses, such as, sodium carboxymethylcellulose; carboxyalkylalkylcelluloses, such as, carboxymethyl ethyl cellulose; carboxyalkylcellulose esters; other natural, semisynthetic, or synthetic polysaccharides, such as, alginic acid, alkali metal and ammonium salts thereof, carrageenans, galactomannans, tragacanth, agar-agar, gum arabicum, guar gum, xanthan gum, starches, pectins, such as sodium carboxymethylamylopectin, chitin derivates such as chitosan, polyfructans, inulin; polyacrylic acids and the salts thereof, polymethacrylic acids and the salts thereof, methacrylate copolymers; vinyl polymers and copolymers such as polyvinyl alcohol, polyvinylpyrrolidone, copolymers of polyvinylpyrrolidone with vinyl acetate, combinations of polyvinyl alcohol and polyvinylpyrrolidone; polyalkylene oxides such as polyethylene oxide and polypropylene oxide and copolymers of ethylene oxide and propylene oxide.

The first polymeric layer may also include hygroscopic or deliquescent materials such as polyethylene glycol, propylene glycol, polypropylene glycol, sodium chloride and other inorganic salts, or any suitable other materials.

Although hydrophilic materials are particularly preferred to be used in this layer, a skilled person will appreciate that inclusion of hydrophobic materials such as ethylcellulose, cellulose acetate and certain acrylates is also possible in the present invention; this and such other modifications are hence apparent and included in the scope of the invention.

The layer may also includes auxiliary agents useful in coating compositions such as plasticizers, pigments, surfactants, fillers, pore-forming agents, anti-foam, anti-tacking agents etc.

In certain preferred embodiments, the layer includes hydrophilic materials such as polyvinyl alcohol, polyvinylpyrrolidone, vinylpyrrolidone-vinyl acetate copolymer and hydroxyalkylcelluloses such as hydroxyethyl cellulose, hydroxypropyl cellulose in the range of from about 10% to about 100% w/w of the layer. The hydrophilic materials are dissolved or dispersed in suitable aqueous solvent systems and layered on the surface of the core till a weight gain of about 2% to about 50% w/w is achieved. Layering is carried out by means of spray coating equipments such as fluid bed coaters and pan coaters. Optionally, auxiliary agents such as plasticizers, anti-tacking agents may also be included in the polymer layer to facilitate smooth processing and manufacturing.

Second Polymeric Layer:

The second polymeric layer (IV) is coated over the first polymeric layer and substantially encapsulates it. It comprises chiefly of polymers which are substantially insoluble in the gastric fluid. The solubility of such polymers may be pH-dependant or pH-independent.

Examples of pH-dependent polymers include enteric cellulose derivatives, enteric acrylic acid-based copolymers, enteric maleic acid-based copolymers, enteric polyvinyl derivatives, zein, shellac, enzymatically degradable polymers etc. Enteric polymers, as will be appreciated by those skilled in the art, are less soluble in the low pH of the gastric fluid and become more soluble in the higher pH environment of the lower gastrointestinal tract or erode slowly as the system passes through the tract. Enzymatically degradable polymers are degraded by microbial enzymes present in the lower gastrointestinal tract, especially the colon. Examples of such polymers include pectin, amylase, chitosan and guar gum.

Specific examples of enteric cellulose derivatives include, but are not limited to, hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose, ethylhydroxyethylcellulose phthalate, etc.

Specific examples of enteric acrylic acid-based copolymers include, but are not limited to, styrene-acrylic acid copolymers, methyl acrylate-acrylic acid copolymers, methyl acrylate-methacrylic acid copolymers, butyl acrylate-styrene-acrylic acid copolymers, methacrylic acid-methyl methacrylate copolymers (for example, product name: Eudragit L100®, Eudragit S®, etc.), methacrylic acid-ethyl acrylate copolymers (for example, product name: Eudragit L100-55®, etc.) methyl acrylate-methacrylic acid-octyl acrylate copolymers, etc.

Specific examples of enteric maleic acid-based copolymers include, but are not limited to, vinyl acetate-maleic anhydride copolymers, styrene-maleic anhydride copolymers, styrene-maleic monoester copolymers, vinyl methyl ether-maleic anhydride copolymers, ethylene-maleic anhydride copolymers, vinyl butyl ether-maleic anhydride copolymers, acrylonitrile-methyl acrylate-maleic anhydride copolymers, butyl acrylate-styrene-maleic anhydride copolymers, etc.

Specific examples of enteric polyvinyl derivatives include, but are not limited to, polyvinyl alcohol phthalate, polyvinyl acetyl phthalate, polyvinyl butyrate phthalate, polyvinyl acetoacetal phthalate, etc.

The above-mentioned gastric or enteric pH-dependent polymers may be used singly or in a combination of two or more coating polymers.

Non-limiting examples of pH independent gastric insoluble polymers include ethylcellulose, cellulose acetate, certain acrylates and similar polymers.

The layer also includes auxiliary agents useful in coating compositions such as plasticizers, pigments, surfactants, fillers, pore-forming agents, anti-foam, anti-tacking agents etc. Alternatively, this layer may also include one or more active agents.

In certain preferred embodiments, the layer constitutes of polymers such as acrylic and methacrylic acid based polymers and copolymers, such as those available under the trade name of Eudragit®, ethylcellulose, cellulose acetate, hydroxypropyl methyl cellulose phthalate and cellulose acetate phthalate. The polymers are present in the range of from about 10% to about 99.9% w/w of the layer. A plasticizer is generally present to reduce the fragility of the coating, and will normally amount to about 1% to about 50% relative to the dry weight of the polymer. Examples of typical plasticizers used include, but are not limited to, triethyl citrate, tributyl citrate, triethyl acetyl citrate, triacetin, diethyl phthalate, dibutyl phthalate and dibutyl sebacate. Optionally, auxiliary agents, such as stabilizers, buffers, colorants, fillers, glidants and anti-foaming agents may also be used. All the components are dissolved/dispersed in suitable solvent systems and coated on the system of the present invention. As will be appreciated by a person skilled in the art, a number of methods are available for polymer coating of a dosage system, e.g., using a conventional coating pan, an airless spray technique, fluid bed coating and the like. The preferred proportion of ingredients and weight gain to be achieved can be readily determined by those skilled in the art by evaluating the desired spatial and/or temporal control and delivery profile required. Preferably, the polymer can be coated in the range from about 5% to about 50% w/w of the system.

In certain preferred embodiments, the second polymeric layer comprises of about 10% to about 100% w/w polymer, about 0% to about 40% w/w plasticizer and about 0% to about 50% w/w anti-tacking agent.

Active Agent Containing Layer:

The active agent containing layer (V) (henceforth referred to as 'active layer') is coated over the second polymeric layer. This layer is applied by spraying a solution or suspension of the active agent over the system. The solvents used for the purpose include aqueous solvents, organic solvents or their mixtures. One or more active agent candidates included in this system are applied as a single layer. Alternatively, this layer is built up by multiple layering where different active agents are applied as different layers or layers with different excipients are alternated with each other.

The active layer can be adapted to provide any desired type of delivery profile of the active agent, which is both spatially and temporally programmable. The system can provide an immediate release delivery profile or modified release delivery profile.

In certain embodiments, the layer is formulated as a matrix type system, wherein the active agent is present in a mixture with a matrix material. The excipients used are commonly known in the art and generally include diluents, binders, stabilizers etc. Rate controlling materials are preferably used when a modified release profile is desired. Rate controlling materials include, for example, various natural and synthetic polymers, gums of plant; animal, mineral or synthetic origin, substituted or unsubstituted hydrocarbons, such as fatty acids, fatty alcohols, glyceryl esters of fatty acids, mineral and vegetable oils and waxes. The type and amount of the material used depends on the nature of modified release desired and is easily determined by the skilled person. For example, typical rate controlling materials which may be used include Hydroxypropyl methyl cellulose, Polyvinyl pyrrolidone, Ethyl cellulose, and Poly(methacrylate) co-polymers.

In certain embodiments, where immediate release is desired, excipients like surfactants such as sodium lauryl sulfate, disintegrants such as croscarmellose sodium etc. may be used.

During manufacturing, an aqueous or a pharmaceutically acceptable solvent medium is used for coating the active agent and one or more excipients on the system. The coating can be applied to the core using any of the coating techniques commonly used in the industry, but fluid bed coating is particularly useful.

In certain embodiments, modified release is achieved by coating a layer of the active agent with a functional coat of rate controlling materials, which modifies the active agent release profile. In such embodiments, it is to be understood that the functional coat of rate controlling materials is considered to be a part of the active layer.

The active layer may contain mucoadhesive substances which may further assist in retention of the system in the gastric region by virtue of their property of adhesion to the gastrointestinal mucosal surface, especially when the fluid levels in the stomach are low. Non-limiting examples of mucoadhesives which may be included are carbopol (various grades), sodium carboxy methylcellulose, methylcellulose, polycarbophil (NOVEON AA-1), hydroxypropyl methylcellulose, hydroxypropyl cellulose, sodium alginate, sodium hyaluronate, and combinations thereof.

In an embodiment, an additional layer is coated on the active layer. It comprises of a hydrophilic material. Such a layer serves the purpose of improving handling characteristics, providing better physical and chemical stability, barrier properties, aesthetic appeal etc. In certain embodiments, such an additional layer, comprising hydrophilic materials, is also coated over the core or the second polymeric layer. A thin film of polymers such as hydroxypropyl methylcellulose (HPMC) (for e.g. Opadry Clear®) may be used for the purpose. While HPMC is typically preferred, other polymers such as hydroxypropylcellulose (HPC) can also be used. Optionally, this layer may include mucoadhesive polymers.

Active Agents:

The active agents encompassed by the invention include any active ingredients which benefit from incorporation into such a system. Examples of such agents include, but are not limited to, active agents used for alzheimer's disease, antibiotics, antiulcers, anti-muscarinic agents, antivirals, anaesthetics, acromegaly agents, steroidal and non-steroidal anti-inflammatory agents, analgesics, antiasthmatics, anticancer agents, anticoagulants and antithrombotic agents, anticonvulsants, antidiabetics antiemetics, alcohol abuse preparations antiglaucoma, antiallergics, antihistamines, anti-infective agents, antiparkinsons, antiplatelet agents, antirheumatic agents, anti spasmodics and anticholinergic agents, antitussives, carbonic anhydrase inhibitors, cardiovascular agents, cholinesterase inhibitors, treatment of CNS disorders, CNS stimulants, contraceptives, cystic fibrosis management, dopamine receptor agonists, endometriosis management, erectile dysfunction therapy, urinary tract disinfectants fertility agents, gastrointestinal agents, immunomodulators and immunosuppressives, vitamins, nutritives, memory enhancers, migraine preparations, muscle relaxants, nucleoside analogues, osteoporosis management, active agents for respiratory organs, parasympathomimetics, prostaglandins, P-gp inhibitors, psychotherapeutic agents, sedatives, hypnotics and tranquillizers, agents used for early morning pathologies, macromolecules such as proteins, polypeptides, polysaccharides, vaccines, antigens, antibodies, active agents used for skin ailments, steroids and hormones and combinations thereof.

Active agents incorporated into the active layer are those that benefit from preferential delivery into the gastric and proximal intestinal regions. Such agents include those having enhanced solubility in the gastric pH, those which are preferentially absorbed through the proximal regions of the gastrointestinal tract, agents having an absorption window in the proximal regions of the gastrointestinal tract, agents having proximal region of the gastrointestinal tract as the local site of action and those that are degraded due to intestinal pH and/or enzymes.

Active agents incorporated into the core compartment are those that benefit from preferential delivery into the distal regions of the gastrointestinal tract. Such agents include those degraded in the acidic pH of the stomach, those having absorption window in the distal regions of the gastrointestinal tract, agents acting locally in the later part of the intestines and for colon delivery of agents which undergo extensive Cytochrome P450 metabolic degradation in small intestine.

Proteins, peptides, macromolecular active agents may also be delivered by incorporation into the core compartment such that they are targeted for release in the colon. In such cases absorption enhancers can also be included in the system to increase the bioavailability of such molecules.

The system also provides for delivery of a combination of active agents, which can be included together or separately in the core and active layer. For example, an embodiment relates to a combination of irinotecan and loperamide. Loperamide is included in the active layer and released immediately, to counter the nausea caused by irinotecan when it is subsequently released from the core.

The system of the invention can also be useful for administration of active agents used in polypill. For example, in an embodiment, agents such as a statin, folic acid and hydrochlorthiazide can be included in the active layer while aspirin, a beta-blocker and an ACE inhibitor can be included in the core compartment.

The system of the invention encompasses delivery of all types of active agents. They may be water soluble or insoluble, high dose or low dose. A complete list of the actives which can be included in the system of the present invention may be obtained from the Merck Index., $14^{th}$ ed., 2006. Generally, an active agent is present in an amount ranging from about 0.5% to about 85% w/w of the system.

Active agents included in certain embodiments include nimesulide, carvedilol, fenofibrate, tacrolimus, baclofen, metformin, loratidine, pseudoephedrine sulfate, bicalutamide, tramadol, leuprolide, enalapril, captopril, benazepril, lisinopril, ranitidine, famotidine, diltiazem, propranolol, verapamil, nifedipine, acyclovir, ciprofloxacin, simvastatin, atorvastatin, dasatinib, pravastatin, lovastatin, selegiline, midazolam, glimepiride; glipizide and nefazodone.

The manufacturing of the system of the present invention is done using processes and equipments commonly used in the manufacture of solid dosage forms. The core of the system is manufactured by blending the appropriate ingredients, optionally including the active agent, preparing granules by wet granulation or dry granulation followed by compression of the granules. Alternatively, the core is manufactured by direct compression or by molding. In case of multiparticulate systems, the cores may be manufactured as small pellets, or pre-formed materials, such as non-pareil seeds may be used. All these processes, including their various modifications, are well known to a person skilled in the art and are included herein by reference.

In certain preferred embodiments, the core thus formed is coated with the first polymeric layer. The first polymeric layer is hydrophilic in nature. A hydrophilic material is dissolved in an aqueous solvent and sprayed onto the pre-warmed cores in a suitable coating equipment, till a weight gain from about 2% to about 50% w/w of the system is achieved. This layer is subsequently coated with the second polymeric layer which contains polymers substantially-insoluble or less soluble in the gastric fluids. A plasticized solution or dispersion of such a polymer is sprayed on the above coated cores till a weight gain of about 5% to about 50% w/w of the system is achieved.

Generation of a positive or negative pressure within the system at this stage causes the expansion of one or more of its compartments, such as expansion of the second polymeric layer, leading to the formation of a hollow space within the system. Positive pressure may be vapor pressure generated due to supply of energy, while negative pressure may be generated due to supply of vacuum.

In certain preferred embodiments, energy, preferably heat is supplied, in the range of about 40° C. to about 150° C., depending on the polymers used. This causes the moisture in the hydrophilic first polymeric layer to evaporate, generating enough positive vapor pressure to exert force on the inner walls of the second polymeric layer. Due to the presence of plasticizers in the second polymeric layer, it has a lower glass transition temperature and a decreased modulus of elasticity. This causes the second polymeric layer to expand, leading to the generation of a hollow space. The supply of energy is done over a period ranging from about a few seconds to about 5 hours.

In certain embodiments, the expansion of the second layer is due to generation of a negative pressure caused by a supply of vacuum. Expansion may also be brought about by a combined supply of energy and vacuum. Although heat is preferred, the use of other types of energies such as microwave energy is also included in the scope of the invention.

The expansion of the compartment/s of the system is preferably plastic expansion. Hence on removal of pressure, at a stage that the second polymeric layer neither collapses, nor cracks, the polymeric layer hardens to provide a hollow space with good structural integrity. During expansion and subsequent hardening of the second polymeric layer, the first polymeric layer may also partially or completely expand and/or migrate, such that after equilibrium, the layer adheres either to the core or to the second polymeric layer or remains independent. As a result the hollow space may be distributed anywhere between the three layers. It may be present either between the first polymeric layer and second polymeric layer, between the core and the first polymeric layer or between all of the three. The space may contain air, vapour, a gas, a mixture of gases or a partial vacuum. The space may be continuous or discontinuous i.e., the layers of the system inside the hollow space may stick to the layers outside the hollow space at single or multiple points.

After hardening of the second polymeric layer, it is then coated with the active layer. A solution or dispersion of the active agent, along with suitable excipients, is sprayed over the system. The active layer is formulated and manufactured as per the active or actives included and the release profile desired.

All the coating processes may be carried out utilizing commonly used equipments such as pan coaters, fluid bed coaters, rotary evaporators, vacuum driers or freeze driers. A person skilled in the art is well versed with the working and functioning of such equipments and can easily obtain the desired results.

The system of the invention thus obtained has a hollow space, generated in-situ, during the manufacturing process. This imparts a low density to the system, such that on ingestion, the system, due to its buoyancy, floats on the gastric fluid. Depending on its formulation, the system can show a gastric retention period of up to 24 hours, say from about one hour to about 24 hours, usually from about 1 hour to about 18 hours, and more commonly up to about 3 to 8 hours. This period is variable, and can be adjusted by varying the excipients and shape and size of the system. During this period, the active agent in the active layer is delivered in the gastric and/or upper intestinal region of the gastrointestinal tract. The second polymeric layer made of polymers substantially insoluble in the gastric fluid, does not dissolve in the gastric conditions and maintains the integrity of the system. As the system reaches the lower part of the gastrointestinal tract and as the pH increases, the second polymeric layer starts to erode or dissolve, exposing the inner hydrophilic layer and core to the gastrointestinal environment. The active agent present in the innermost core is then delivered in the lower intestinal and/or the colonic region as per the desired release profile. Optionally the core may not contain any active agent.

The size and shape of a gastric retention system can affect its gastric residence time. The system of the invention can be tailored to a suitable size and shape as per the characteristics desired. The system of the invention may preferably be in the form of shapes such as round, oval, capsule shaped, spherical, cylindrical, triangular, square, rectangular or polygonal. Multiparticulate systems may be filled into capsules for release into the gastric cavity, or compressed or molded into unit dosage forms. The size of the system is also an important formulation parameter. Generally, medium sized systems, such as with a diameter of around 7 to 8 mm are found to show a better gastric residence as compared to larger tablets. The system of the invention can be suitably sized.

The system of the present invention can be programmed to provide any desired type of active agent delivery profile. The system can be programmed to provide both spatial and temporal controlled active agent release. The system can be an immediate or a modified release system According to an embodiment of the invention, the system is formulated such that the core is a placebo i.e. contains no active agent. The system delivers the active agent from the active agent containing layer to the gastric and/or upper intestinal regions.

In an embodiment, the active agent delivery from the above mentioned system is substantially immediate.

In another embodiment the active agent delivery from the above mentioned system is by modified release.

As a further embodiment, the modified release from the above mentioned system is controlled by diffusion through or erosion of a matrix.

As an alternate embodiment, the modified release from the above mentioned system is controlled by application of a functional coating.

According to an embodiment of the invention, the system is formulated to contain an active agent in the core in addition to the active layer. Such a system delivers the active agent from the active layer to the gastric and/or upper intestinal regions and the active agent in the core compartment to the lower intestinal and/or colonic regions of the gastrointestinal tract.

The delivery is thus in a pulsatile manner, one pulse released immediately on administration and the other after a predetermined delay. In different embodiments, one or both of the pulses may be modified release pulses.

In some embodiments, the same active agent is included both in the core and the active layer.

In other embodiments, different active agents are included in the core and the active layer.

In certain embodiments of the invention, the system is formulated such that there is no active agent containing layer coated over the polymeric layer. Thus the system comprises of a core, one or more polymeric layers coated over the core and a preformed hollow space. The active agent is present in the core and is delivered in the lower intestinal and/or the colonic region when the system is administered orally. The release may be immediate or modified.

In an alternative embodiment, the first polymeric layer is absent, and the hydrophilic material contained therein is incorporated within the core. The core may then be manufactured to contain high percentages of moisture and also such that its surface has low adherence to the overlying polymeric layer. Thus the system comprises of a core comprising a hydrophilic material, a polymeric layer comprising a polymer substantially insoluble in the gastric fluid, an active agent containing layer and a preformed hollow space which is present substantially between the core and the polymeric layer.

Any such and other modifications which would be obvious to a person skilled in the art based upon the disclosure herein, and which fall within the spirit and scope of the invention, are also considered to be included within the invention.

As is clear from the above description, the system of the invention demonstrates following advantages:

The system of the invention has a preformed hollow space. It does not require the gastric fluid to activate its floatation mechanism. Thus it is substantially independent of the gastric conditions for its proper functioning. The system is sophisticated, yet simple, functionally reproducible and upscalable. It is easy to manufacture, amenable to large scale production, does not require sophisticated equipments and uses common raw materials which are biodegradable, non-toxic and biocompatible.

The system is also flexible with regards to formulation and can be spatially and temporally programmed to exhibit any type of desired active agent release profile. It can provide for delivery of two different active agent candidates having different region-selective absorption windows through a single system. It is versatile regarding the type of active agent which can be incorporated therein; the active agent may be water soluble or insoluble, low dose or high dose.

The system can also provide continuous input of an active agent in the gastric region, resulting in plasma concentration profiles in a narrow range, and less fluctuations in plasma levels, which is of special significance for narrow therapeutic index agents.

Various modifications of the system of the invention may be made without departing from the spirit or scope of the invention. The following non-limiting examples illustrate various embodiments of the invention and should not be construed to limit the scope of the invention.

EXAMPLES 1 TO 8

TABLE 1

| Ingredient | 1 | 2 | 3 | 4 | 5 | 6 | 7 | 8 |
|---|---|---|---|---|---|---|---|---|
| | | | | Qty (%) | | | | |
| Core | | | | | | | | |
| Lactose monohydrate | — | 50.0 | 40.0 | — | — | 78.0 | 80.0 | 79.0 |
| Cellulose microcrystalline | 59.0 | 20.0 | 43.5 | 83.5 | 59.0 | — | 19 | — |
| Starch | 30.0 | 29.5 | — | — | 30.0 | — | — | — |
| Polyvinyl pyrrolidone | — | — | — | 15.0 | — | 20.0 | — | 20.0 |
| Xanthan gum | 10.0 | — | 15.0 | — | 10.0 | — | — | — |
| Purified water | q.s. | q.s. | q.s. | q.s. | q.s. | q.s. | — | q.s. |
| Colloidal silicondioxide | — | — | 0.5 | 0.5 | — | — | 0.5 | — |
| Magnesium stearate | 1.0 | 0.5 | — | 1.0 | 1.0 | — | 0.5 | 1.0 |
| Glyceryl behenate | — | — | 1.0 | — | — | 2.0 | — | — |
| First Polymeric layer | | | | | | | | |
| Polyvinyl pyrrolidone (Povidone) | — | 10.0 | — | — | — | 15.0 | 15.0 | — |
| Hydroxypropyl methyl cellulose | — | — | 20.0 | — | 15.0 | — | — | 15.0 |
| Vinyl acetate/vinyl pyrrolidone co-polymer 60/40 | — | — | — | 15.0 | — | — | — | — |
| Poly(methyl vinyl ether/maleic anhydride) | 15.0 | — | — | — | — | — | — | — |
| Isopropyl alcohol | — | q.s. | — | — | — | — | q.s. | — |
| Ethanol | q.s. | — | — | — | — | — | — | — |
| Purified water | — | q.s. | q.s. | q.s. | q.s. | q.s. | — | q.s. |
| Second polymeric layer | | | | | | | | |
| poly(methacrylic acid, methyl methacrylate) 1:2 | — | 24.0 | — | — | 24.0 | — | 16.34 | 24.0 |
| Poly(methacrylic acid, methyl methacrylate) 1:1 | — | — | — | 28.0 | — | — | 7.0 | — |
| Triethyl citrate | — | 7.0 | — | 8.0 | 7.0 | — | 7.0 | 7.0 |
| Poly(methacrylic acid, ethyl acrylate) 1:1 | — | — | — | — | — | 22.5 | — | — |
| Ethyl cellulose | — | — | 35.0 | — | — | — | — | — |
| Cellulose acetate | 25.67 | — | — | — | — | — | — | — |
| Hydroxypropyl methyl cellulose phthalate | — | — | — | — | — | — | — | — |
| Acetyl tributyl citrate | — | — | 7.0 | — | — | — | — | — |
| Polyethylene glycol | 7.7 | | | | | | | |

TABLE 1-continued

| Ingredient | 1 | 2 | 3 | 4 | 5 | 6 | 7 | 8 |
|---|---|---|---|---|---|---|---|---|
| | | | | Qty (%) | | | | |
| Acetone | q.s. | q.s | q.s. | q.s | q.s | — | q.s | q.s |
| Isopropyl alcohol | — | q.s | — | — | q.s | — | q.s | q.s |
| Purified water | — | q.s | — | — | q.s | q.s. | q.s | q.s |
| Talc | — | 11.67 | — | 11.67 | 11.67 | — | 11.67 | 11.67 |

EXAMPLES 9 TO 15

TABLE 2

| Ingredient | 9 | 10 | 11 | 12 | 13 | 14 | 15 |
|---|---|---|---|---|---|---|---|
| | | | | Qty (%) | | | |
| Core | | | | | | | |
| Lactose monohydrate | — | — | 82.5 | 54.0 | — | — | 51.0 |
| Cellulose microcrystalline | 81.5 | 95.5 | — | 25.0 | 81.5 | 96.0 | 30.0 |
| Starch | — | — | — | — | — | — | — |
| Polyvinyl pyrrolidone | 15.0 | — | — | 20.0 | 15.0 | — | 15.0 |
| Xanthan gum | — | — | 15.0 | — | — | — | — |
| Purified water | q.s. | — | q.s. | q.s. | q.s. | — | q.s. |
| Colloidal silicondioxide | 1.0 | 2.0 | — | — | 1.0 | 2.0 | 1.0 |
| Magnesium stearate | 0.5 | 1.0 | 1.0 | 1.0 | 0.5 | — | 1.0 |
| Glyceryl behenate | 2.0 | 1.5 | 1.5 | — | 2.0 | 2.0 | 2.0 |
| First Polymeric layer | | | | | | | |
| Polyvinyl pyrrolidone (Povidone) | — | — | 15.0 | — | — | 10.0 | — |
| Hydroxypropyl methyl cellulose | — | 15.0 | — | 20.0 | — | — | 20.0 |
| Vinyl acetate/vinyl pyrrolidone co-polymer 60/40 | 15.0 | — | — | — | 15.0 | — | — |
| Poly(methyl vinyl ether/maleic anhydride) | — | — | — | — | — | — | — |
| Isopropyl alcohol | — | — | q.s. | — | — | q.s. | — |
| Ethanol | — | — | — | — | — | — | — |
| Purified water | q.s. | q.s. | — | q.s. | q.s. | — | q.s. |
| Second polymeric layer | | | | | | | |
| poly(methacrylic acid, methyl methacrylate) 1:2 | — | — | — | — | 24.0 | — | — |
| Poly(methacrylic acid, methyl methacrylate) 1:1 | — | — | 28.0 | — | — | — | — |
| Triethyl citrate | — | — | 8.0 | — | 7.0 | — | — |
| Poly(methacrylic acid, ethyl acrylate) 1:1 | — | 35.2 | — | — | — | — | — |
| Ethyl cellulose | — | — | — | — | — | 35.0 | — |
| Cellulose acetate | — | — | — | — | — | — | 38.25 |
| Hydroxypropyl methyl cellulose phthalate | 27.8 | — | — | 27.8 | — | — | — |
| Acetyl tributyl citrate | — | — | — | — | — | 7.0 | — |
| Polyethylene glycol | — | — | — | — | — | — | 9.56 |
| Acetone | — | — | q.s | — | q.s | q.s. | q.s. |
| Isopropyl alcohol | — | — | — | — | q.s | — | — |
| Purified water | q.s. | q.s. | — | q.s. | q.s | — | — |
| Talc | — | — | 11.67 | — | 11.67 | — | — |

Examples 1 to 15 illustrate different compositions of the core, first polymeric layer and second polymeric layer of the system of the present invention. The ingredients of the core are sifted and blended. In case of wet granulation, the binder polyvinyl pyrrolidone or xanthan gum is dissolved in purified water and added to the blend till a granulation end point is reached. The granules are dried, blended with glidant/lubricant and then compressed on a rotary tablet compression machine into core tablets. In case of examples 7, 10 and 14, the ingredients are sifted, blended and then directly compressed into core tablets.

The core tablets obtained in each case are pre-warmed in suitable coating equipment. A solution of the polymer in the solvent is sprayed on the tablets and coating is carried out till the desired weight gain is achieved, a maximum of about 50% w/w weight gain, to form the first polymeric layer. For the second polymeric layer, a solution/dispersion of the ingredients such as the polymer, plasticizer and anti-glidant (as mentioned in the examples given in Tables 1 and 2) is coated on the pre-heated tablets till a desired weight gain is achieved, a maximum of about 50% w/w is achieved.

Hot air (about 40° C. to about 150° C.) is applied to the coated tablets till about 2 hours, which causes expansion and hardening of the polymeric layer. Subsequent cooling leads to the formation of an integral hollow space within the system, and decreases the density of the system.

EXAMPLE 16

TABLE 3

| Ingredient | Qty (mg/tab) A | Qty (mg/tab) B | Qty (mg/tab) C | Qty (mg/tab) D |
|---|---|---|---|---|
| Carvedilol | 6.25 | 6.25 | 6.25 | 6.25 |
| Polyvinyl pyrrolidone | 15.0 | 25.0 | 20.83 | 30.0 |
| Polyethylene glycol | 3.125 | 6.25 | 3.125 | 6.25 |
| Ethyl cellulose | 12.45 | 6.35 | 6.21 | 12.45 |
| Dibutyl sebacate | 6.22 | 3.17 | 3.102 | 6.22 |
| Polyvinyl pyrrolidone | 6.51 | 7.0 | 6.51 | 8.5 |
| Purified water # | q.s. | q.s. | q.s. | q.s. |

Not present in final product

Carvedilol was suspended in aqueous solution of polyvinyl pyrrolidone and polyethylene glycol and loaded on any of the preformed hollow systems mentioned in examples 1 to 15, in suitable coating equipment. Ethyl cellulose was mixed with Dibutyl sebacate and polyvinyl pyrrolidone and coated onto the active agent loaded system. The system was further subjected to drying.

Figure 2:
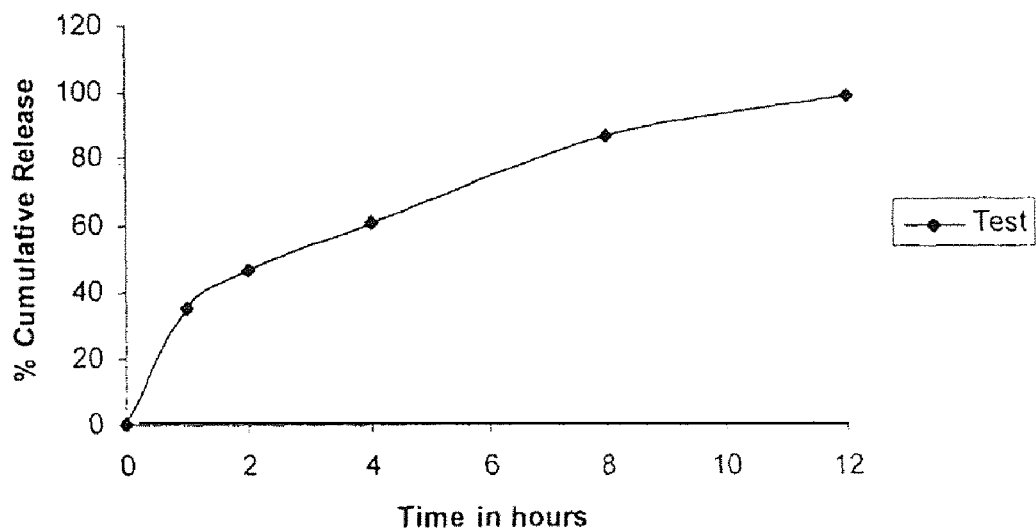
FIG. 2 shows the dissolution profile of Carvedilol ("Test") from Example 16C.

The system was subjected to dissolution studies in 900 ml of simulated gastric fluid at 37° C., in USP apparatus Type II, 50 rpm. As observed in the FIG. 2, Test product exhibited a prolonged release over a period of about 12 hrs.

EXAMPLE 17

TABLE 4

| Ingredient | Qty (mg/tab) A | Qty (mg/tab) B | Qty (mg/tab) C | Qty (mg/tab) D | Qty (mg/tab) E |
|---|---|---|---|---|---|
| Metformin hydrochloride | 500.0 | 500.0 | 500.0 | 500.0 | 500.0 |
| Ethyl cellulose | 150.0 | 175.0 | 200.0 | 250.0 | 300.0 |
| Dibutyl sebacate | 34.5 | 40.25 | 47.94 | 62.5 | 75.0 |
| Purified water # | q.s. | q.s. | q.s. | q.s. | q.s. |

Not present in final product

Dibutyl sebacate was mixed with Ethyl cellulose dispersion. Metformin hydrochloride was dissolved in purified water and added to above dispersion and then loaded on the preformed hollow systems mentioned in examples 1 to 15, in suitable coating equipment.

Figure 3:
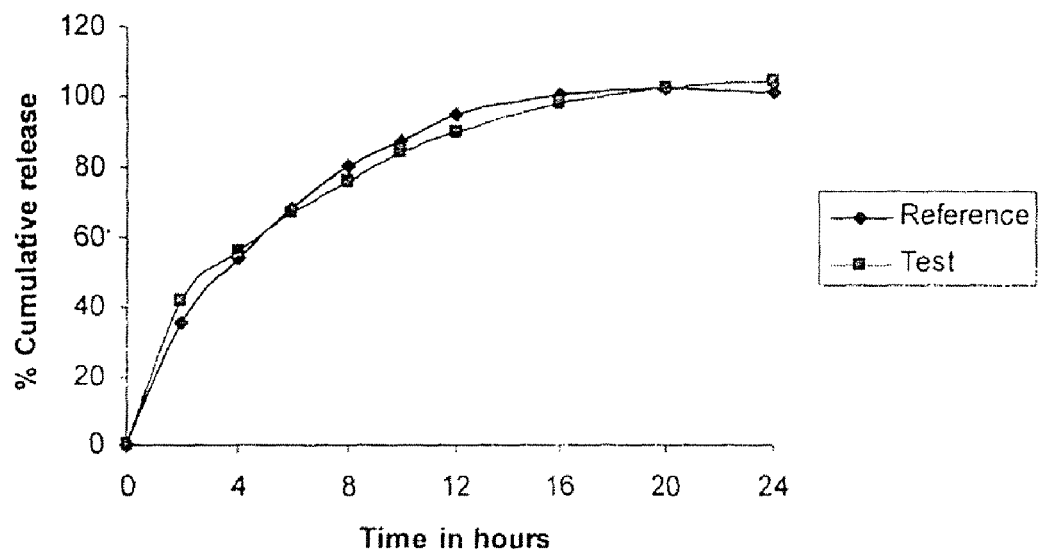
FIG. 3 shows the dissolution profile of Metformin ("Test") from Example 17C, in comparison with dissolution profile of Glumetza® 500 mg ("Reference").

The system was subjected to dissolution studies in similar conditions as mentioned in Example 16. The dissolution profile was compared with Reference Giumetza® 500 mg. As observed in the FIG. 3, the Test product exhibited comparable release as the reference product.

EXAMPLE 18

TABLE 5

| Ingredient | Qty (mg/tab) A | Qty (mg/tab) B | Qty (mg/tab) C | Qty (mg/tab) D | Qty (mg/tab) E |
|---|---|---|---|---|---|
| Fenofibrate | 145.0 | 145.0 | 145.0 | 145.0 | 145.0 |
| Sodium lauryl sulfate | 2.9 | 3.0 | 4.0 | 3.5 | 4.5 |
| Polyvinyl pyrrolidone | 145.0 | 145.0 | 145.0 | 72.5 | 72.5 |
| Polyethylene glycol | 29.0 | 30.0 | 40.0 | 35.0 | 45.0 |
| Purified water # | q.s. | q.s. | q.s. | q.s. | q.s. |

Not present in final product

Sodium lauryl sulfate, polyvinyl pyrrolidone and polyethylene glycol were dissolved in water. Fenofibrate was added to above solution and mixed. The resulting mixture was loaded on any of the preformed hollow systems mentioned in examples 1 to 15, in suitable coating equipment.

Figure 4:
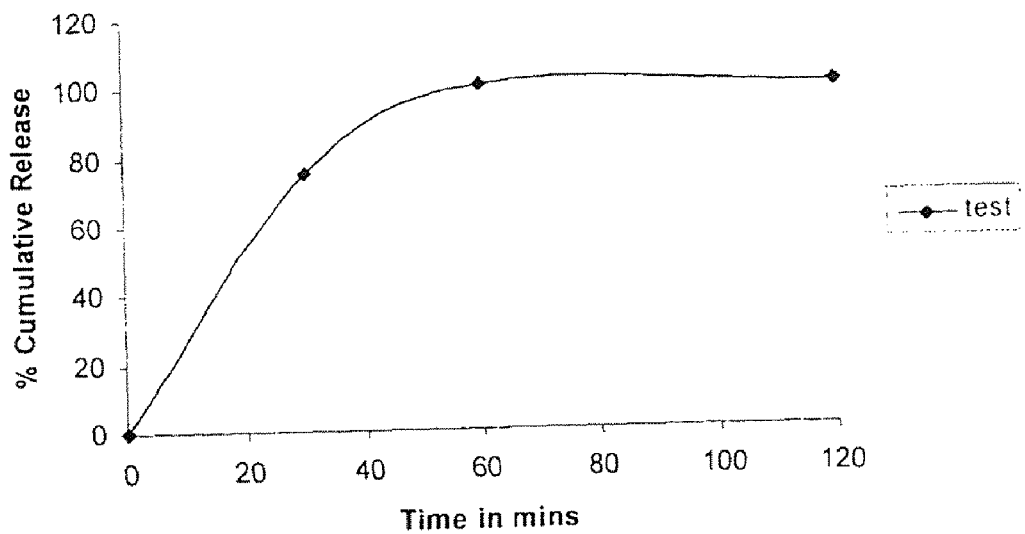
FIG. 4 shows the dissolution profile of Fenofibrate ("Test") from Example 18C

The system was subjected to dissolution studies in 900 ml of 0.05M sodium lauryl sulfate at 37° C., in USP apparatus Type II, 75 rpm. A complete dissolution of the hydrophobic fenofibrate was observed within an hour as shown in FIG. 4.

EXAMPLE 19

TABLE 6

| Ingredient | Qty (mg/tab) A | Qty (mg/tab) B | Qty (mg/tab) C | Qty (mg/tab) D |
|---|---|---|---|---|
| Inner layer | | | | |
| Pseudoephedrine sulfate | 240.0 | 240.0 | 240.0 | 240.0 |
| Ethyl cellulose | 90.0 | 80.0 | 70.0 | 60.0 |
| Acetyl Tributyl citrate | 22.5 | 20.0 | 21.0 | 18.0 |
| Povidone | 15.0 | 16.0 | 17.5 | 18.0 |
| Purified water # | q.s. | q.s. | q.s. | q.s. |
| Outer layer | | | | |
| Loratidine | 10.0 | 10.0 | 10.0 | 10.0 |
| Polyvinyl pyrrolidone | 5.0 | 5.0 | 10.0 | 15.0 |
| Polyethylene glycol | 1.5 | 1.5 | 3.0 | 4.5 |
| Purified water # | q.s. | q.s. | q.s. | q.s. |

Not present in final product

Inner layer: Ethyl cellulose dispersion was mixed with acetyl tributyl citrate and povidone in water. Pseudoephedrine sulfate was mixed with the above and loaded on the preformed hollow systems mentioned in examples 1 to 15, in suitable coating equipment.

Outer layer: Polyvinyl pyrrolidone was dissolved in water and polyethylene glycol was added. Loratidine was subsequently added and mixed. The solution was then sprayed onto the pseudoephedrine loaded system in suitable coating equipment to get a bilayer product.

Figure 5:
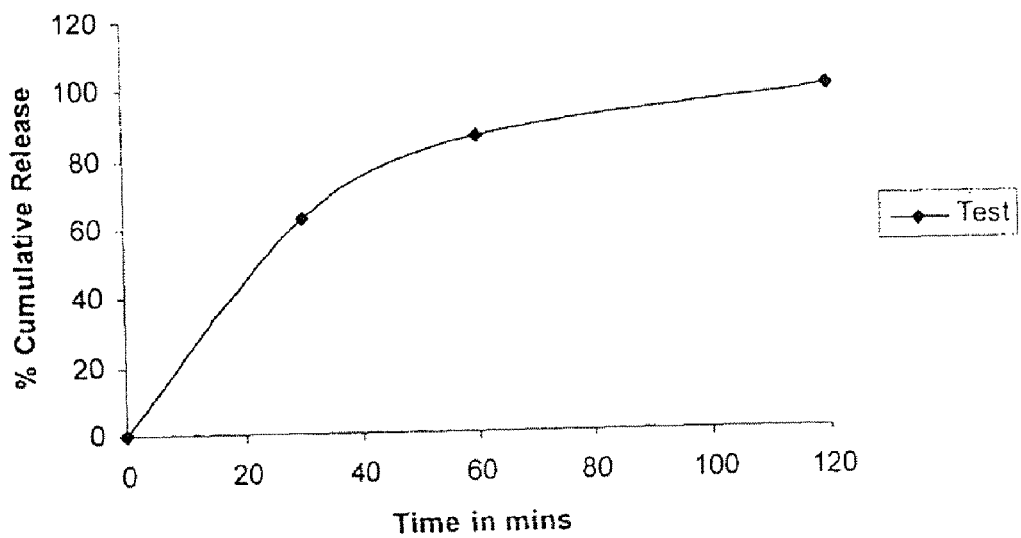
FIG. 5 shows the dissolution profile of Loratidine ("Test") from Example 19B.
Figure 6:
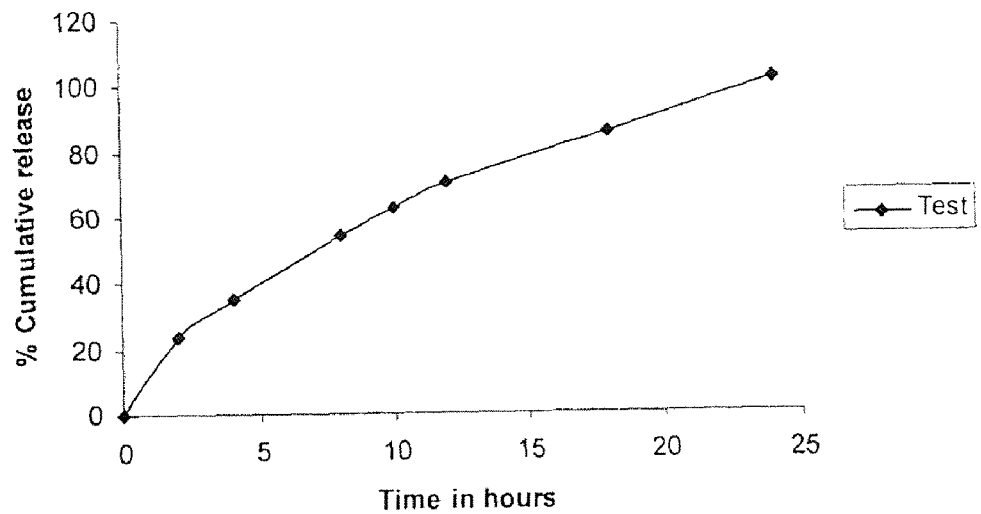
FIG. 6 shows the dissolution profile of Pseudoephedrine ("Test") from Example 19B.

Dissolution profiles of both the active agents have been depicted in FIGS. 5 and 6. As observed, Loratidine demonstrates immediate release within 2 hours, while Pseudoephedrine is released in a modified manner, over a period of 24 hours.

EXAMPLE 20

TABLE 7

| Ingredient | Qty (mg/tab) A | Qty (mg/tab) B | Qty (mg/tab) C | Qty (mg/tab) D | Qty (mg/tab) E |
|---|---|---|---|---|---|
| Baclofen | 40.0 | 40.0 | 40.0 | 40.0 | 40.0 |
| Povidone | 5.0 | 2.5 | 7.0 | 10.0 | 2.0 |
| Polyethylene glycol | 1.0 | 0.5 | 1.4 | 2.0 | 2.0 |
| Sodium lauryl sulfate | 0.08 | 0.1 | 0.4 | 0.2 | 0.2 |
| Purified water # | q.s. | q.s. | q.s. | q.s. | q.s. |
| Poly(methacrylate) co-polymer | 25.5 | 30.0 | 20.5 | 35.2 | 40.0 |
| Purified water # | q.s. | q.s. | q.s. | q.s. | q.s. |

Not present in final product

Baclofen was dissolved in povidone, sodium lauryl sulfate and polyethylene glycol solution in purified water. The solution was loaded on the preformed hollow systems mentioned in examples 1 to 15, in suitable coating equipment. The baclofen loaded cores were further coated with poly methacrylate co-polymer dispersion in suitable coating equipment. The coated tablets were dried at suitable temperature for a period of 2 hours.

Figure 7:
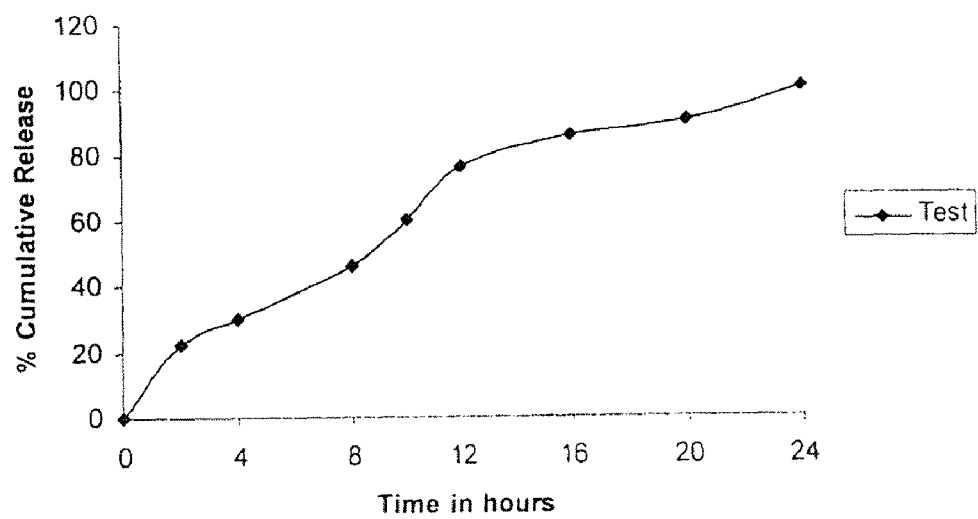
FIG. 7 shows the dissolution profile of Baclofen ("Test") from Example 20C.

The system was subjected to dissolution studies in 900 ml of Simulated Gastric Fluid at 37 C, in USP apparatus Type II, 50 rpm. The system exhibited prolonged release over a period of about 24 hrs, as seen in FIG. 7.

EXAMPLE 21

TABLE 8

| Ingredient | Qty (mg/tab) A | Qty (mg/tab) B | Qty (mg/tab) C | Qty (mg/tab) D |
|---|---|---|---|---|
| Core | | | | |
| Leuprolide acetate | 1.0 | 1.0 | 1.0 | 1.0 |
| Microcrystalline cellulose | 93.0 | 94.0 | 94.5 | 93.5 |
| Croscarmellose sodium | 4.0 | 3.0 | 3.0 | 3.5 |
| Magnesium stearate | 2.0 | 2.0 | 1.5 | 2.0 |
| First polymeric layer | | | | |
| Polyvinyl pyrrolidone | 15.0 | 15.0 | 20.0 | 25.0 |
| Isopropyl alcohol | q.s. | q.s. | q.s. | q.s. |
| Second polymeric layer | | | | |
| Poly(methacrylic acid, methyl methacrylate) | 25.5 | 35.0 | 40.0 | 45.0 |
| Acetone # | q.s. | q.s. | q.s. | q.s. |
| Isopropyl alcohol # | q.s. | q.s. | q.s. | q.s. |
| Purified water # | q.s. | q.s. | q.s. | q.s. |
| Triethyl citrate | 8.92 | 12.25 | 14.0 | 15.75 |
| Talc | 10.25 | 17.5 | 20.0 | 22.5 |
| Active agent containing layer | | | | |
| Bicalutamide | 50.0 | 50.0 | 50.0 | 50.0 |
| Polyvinyl pyrrolidone | 5.0 | 3.0 | 4.0 | 4.5 |
| Polyethylene glycol | 1.0 | 0.6 | 0.8 | 0.9 |
| Purified water # | q.s. | q.s. | q.s. | q.s. |

Not present in final product.

Leuprolide acetate was mixed with microcrystalline cellulose and further blended with croscarmellose sodium and magnesium stearate. The blend was compressed into tablets on a rotary tablet compression machine to form the cores. The cores thus obtained were pre-warmed and coated with polyvinyl pyrrolidone solution in suitable coating equipment, to form the first polymeric layer. The system was further coated with acrylic acid co-polymer plasticized solution in acetone and isopropyl alcohol in coating equipment to form the second polymeric layer.

Hot air (about 40° C. to 150° C.) was applied to the coated tablets for about 1.5 hours, which caused expansion and hardening of the polymeric layer. Subsequent cooling lead to the formation of a hollow space within the system.

Bicalutamide in polyvinyl pyrrolidone and polyethylene glycol solution was loaded onto the system in the coating equipment to form the active layer.

Figure 8:
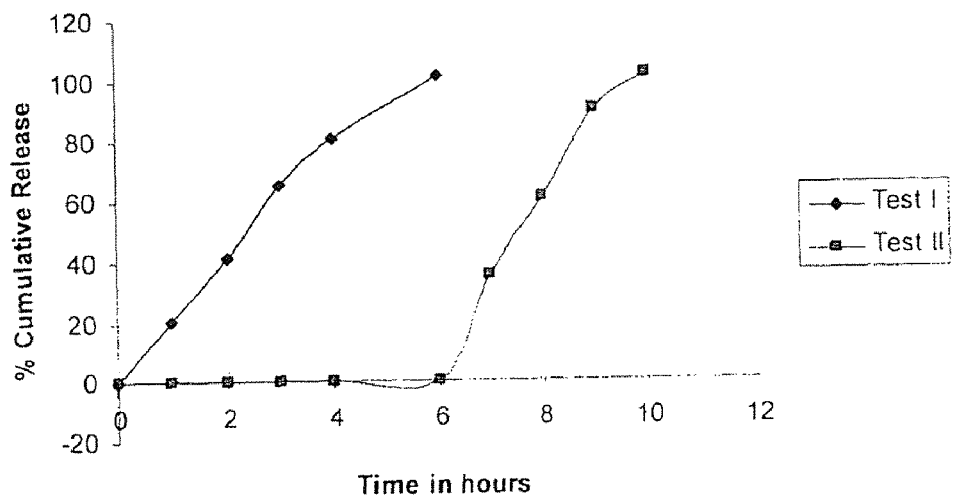
FIG. 8 shows the dissolution profiles of Bicalutamide ("Test I") and Leuprolide ("Test II") from Example 21A.

The system was subjected to dissolution studies by using the following pH change method: pH 1.2 (750 ml) 2 hrs, pH 4.5-1 hr, pH 6.8-3 hr and pH 7.4 buffer in sodium lauryl sulfate (1000 ml), at 37° C., USP Apparatus Type II, 75 rpm. As seen from FIG. 8, Bicalutamide was released within four hours (Test 1), while release of Leuprolide, which was included in the core, commenced after 6 hours and was released till 10 hours (Test II).

EXAMPLE 22

TABLE 9

| Ingredient | Qty (mg/tab) A | Qty (mg/tab) B | Qty (mg/tab) C | Qty (mg/tab) D |
|---|---|---|---|---|
| Core | | | | |
| Tacrolimus | 2.5 | 2.5 | 2.5 | 2.5 |
| Hydroxypropyl methyl cellulose | 2.6 | 3.0 | 2.5 | 3.0 |
| Dichloromethane # | q.s. | q.s. | q.s. | q.s. |
| Ethanol # | q.s. | q.s. | q.s. | q.s. |
| Lactose | 89.9 | 89.0 | 90.5 | 89.0 |
| Croscarmellose sodium | 3.0 | 3.5 | 3.0 | 4.0 |
| Magnesium stearate | 2.0 | 2.0 | 1.5 | 1.5 |
| First polymeric layer | | | | |
| Polyvinyl pyrrolidone | 15.0 | 15.0 | 20.0 | 25.0 |
| Purified water | q.s. | q.s. | q.s. | q.s. |
| Second polymeric layer | | | | |
| Poly(methacrylic acid, methyl methacrylate) | 25.5 | 35.0 | 40.0 | 45.0 |
| Acetone # | q.s. | q.s. | q.s. | q.s. |
| Isopropyl alcohol # | q.s. | q.s. | q.s. | q.s. |
| Purified water # | q.s. | q.s. | q.s. | q.s. |
| Triethyl citrate | 8.92 | 12.25 | 14.0 | 15.75 |
| Talc | 10.25 | 17.5 | 20.0 | 22.5 |
| Active agent containing layer | | | | |
| Tacrolimus | 2.5 | 2.5 | 2.5 | 2.5 |
| Hydroxypropyl methyl cellulose | 2.6 | 3.0 | 2.5 | 3.0 |
| Dichloromethane # | q.s. | q.s. | q.s. | q.s. |
| Ethanol # | q.s. | q.s. | q.s. | q.s. |

Not present in final product

Tacrolimus was dissolved in a solution of hydroxypropyl methyl cellulose in dichloromethane and ethanol. The mixture was loaded onto part of lactose powder and dried to remove solvents. The above mixture was then blended with remaining lactose, croscarmellose sodium and magnesium stearate. The blend was compressed into tablets on a rotary tablet compression machine to form the cores.

The cores thus obtained were pre-warmed and coated with polyvinyl pyrrolidone solution in suitable coating equipment, to form the first polymeric layer. The system was further coated with acrylic acid co-polymer plasticized solution in acetone and isopropyl alcohol in coating equipment to form the second polymeric layer.

Hot air (40° C. to 150° C.) was applied to the coated tablets for about 4 hours, which caused expansion and hardening of the polymeric layer. Subsequent cooling lead to the formation of a hollow space within the system.

The solution of tacrolimus and hydroxypropyl methyl cellulose in dichloromethane and ethanol was loaded onto the above tablets in suitable coating equipment to form the active layer.

Figure 9:
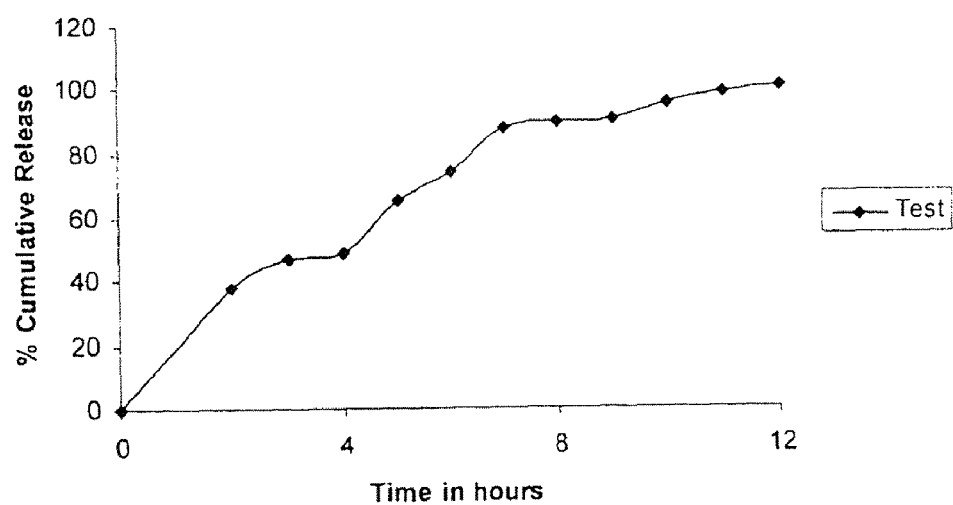
FIG. 9 shows the dissolution profile of Tacrolimus ("Test") from Example 22B.

The system was subjected to dissolution studies by using the following pH change method: pH 1.2-2 hrs, pH 4.5-1 hr, pH 6.8-1 hr and pH 7.4 buffer at 37° C., USP Apparatus Type II, 75 rpm. As seen from FIG. 9, Tacrolimus was released over a period of 12 rs.

EXAMPLE 23

TABLE 10

| Ingredient | Qty (mg/tab) |
|---|---|
| Core | |
| Lactose monohydrate | 80.0 |
| Microcrystalline cellulose | 19.0 |
| Magnesium stearate | 1.0 |

TABLE 10-continued

| Ingredient | Qty (mg/tab) |
|---|---|
| Active agent containing layer | |
| Baclofen | 10.0 |
| polyvinyl pyrrolidone | 3.0 |
| Total | 13.0 |

Lactose monohydrate and microcrystalline cellulose were mixed together in a suitable blender. Magnesium stearate was further blended with the above powder mix. The mixture was compressed on a rotary tablet compression machine to form core tablets of 100 mg weight. The tablets were coated with an aqueous/non-aqueous solution of vinylpyrrolidone-vinyl acetate copolymer. Further coating was applied with acrylate polymers/co-polymers (Eudragit L-100+Eudragit S-100) with triethyl citrate as plasticizer in acetone/isopropyl alcohol mixture. The coated tablets were subjected to heating at temperatures ranging from 40° C. to 150° C. On expansion of the coated layer, the heat was removed and tablets were sprayed with an aqueous solution of baclofen and polyvinyl pyrrolidone.

EXAMPLE 24

TABLE 11

Test 1

| No. | Ingredient | Qty (mg/tab) A | Qty (mg/tab) B | Qty (mg/tab) C | Qty (mg/tab) D | Qty (mg/tab) E |
|---|---|---|---|---|---|---|
| 1 | Nimesulide | 150.00 | 150.00 | 150.00 | 150.00 | 150.00 |
| 2 | Hydroxypropyl methyl cellulose | 30.0 | 22.62 | 33.25 | 20.55 | 42.5 |
| 3 | Polyethylene glycol | 4.5 | 3.39 | 6.65 | 4.11 | 6.37 |
| 4 | Purified water # | q.s. | q.s | q.s. | q.s. | q.s. |

Not present in final product

TABLE 12

Test 2

| No. | Ingredient | Qty (mg/tab) A | Qty (mg/tab) B | Qty (mg/tab) C | Qty (mg/tab) D | Qty (mg/tab) E |
|---|---|---|---|---|---|---|
| 1 | Nimesulide | 200.00 | 200.00 | 200.00 | 200.00 | 200.00 |
| 2 | Hydroxypropyl methyl cellulose | 33.25 | 20.55 | 29.99 | 35.52 | 40.25 |
| 3 | Polyethylene glycol | 4.98 | 4.11 | 4.49 | 5.32 | 8.05 |
| 4 | Purified water # | q.s. | q.s. | q.s | q.s. | q.s. |

Not present in final product

Hydroxypropyl methyl cellulose, polyethylene glycol and nimesulide were dissolved in purified water. The solution was loaded on a preformed hollow system mentioned in examples 1 to 15, in suitable coating equipment.

The systems were subjected to dissolution studies in 0.001N HCl in 1% SLS at 37° C., USP Apparatus Type II, 75 rpm. The dissolution of the test systems were compared with the reference Aulin® tablets 200 mg. As observed in the following Table 13, while the reference showed complete dissolution within 15 mins, both the Test systems (Test 1B and Test 2C) demonstrated prolonged release over a period of about 6 hours.

TABLE 13

| Time | Cumulative % release | | |
|---|---|---|---|
| (hrs) | Test IB | Test IIC | Reference |
| 0 | 0.0 | 0.0 | 0 |
| 1 | 17.0 | 15.3 | 102 |
| 2 | 38.6 | 23.8 | |
| 3 | 60.1 | 37.0 | |
| 4 | 79.2 | 51.8 | |
| 5 | 90.9 | 71.7 | |
| 6 | 99.1 | 94.3 | |
| 7 | 101.5 | 97.7 | |
| 8 | | 100.1 | |

Biostudy in Human Volunteers:

Title: A randomized, open label, balanced, three-treatment, three-period, three-sequence, single dose, crossover bioequivalence study of nimesulide 150 mg tablets (Test 1B), and nimesulide 200 mg tablets (Test 2C), with Aulin® (nimesulide 100 mg) 2 tablets (Reference product) of Helsinn Healthcare SA, Switzerland, in six healthy, adult, male, human subjects under fed conditions.

Blood Sampling In each period, a total of 12 blood samples (5 ml each) were collected. First sample was collected within 1 hour prior to drug administration (0.0 hour) and subsequent samples were collected at 0.5, 1.0, 2.0, 3.0, 4.0, 6.0, 8.0, 12.0, 16.0, 20.0 and 24.0 hours after drug administration.

Pharmacokinetic Parameters Pharmacokinetic analysis was performed on plasma concentration and time data of nimesulide using non-compartmental model of WinNonLin® Enterprise version 5.0.1. Pharsight USA. The following pharmacokinetic parameters were calculated. $C_{max}$, $AUC_{0-t}$, $AUC_{0-\infty}$, $T_{max}$, Kel and $t_{1/2}$ Analytical Assay: Plasma concentration of nimesulide was measured by a validated analytical method using LC-MS/MS.

Statistical Analysis Statistical analysis was performed on the pharmacokinetic parameters by using SAS® statistical software (Version: 9.1; SAS Institute Inc., USA).

Figure 10:
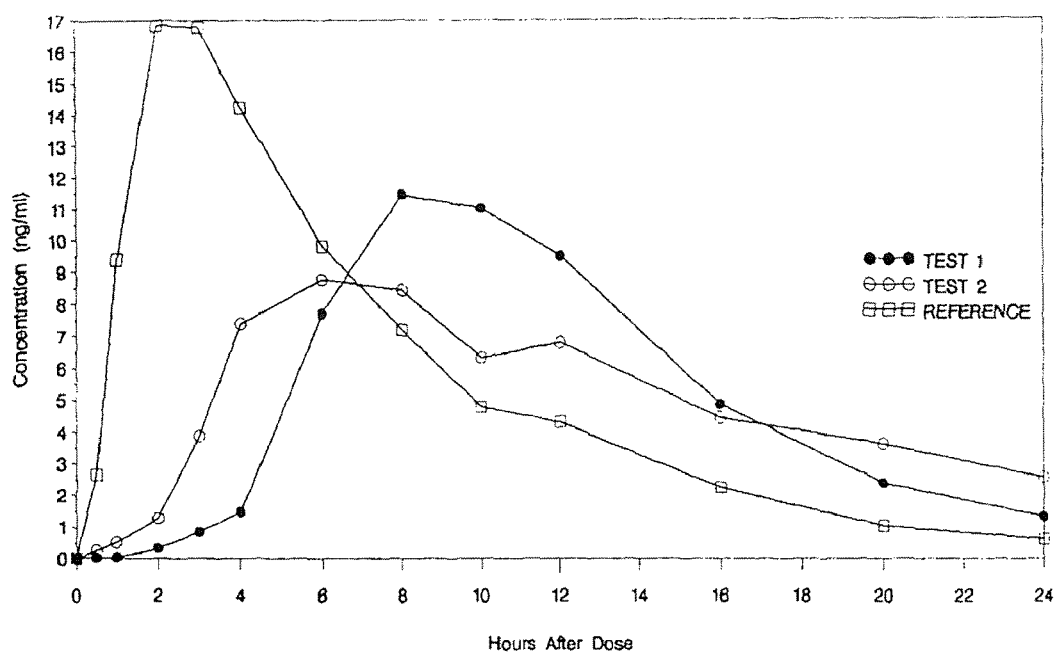
FIG. 10 shows the graphical comparison of the dose normalized plasma concentration time profiles of the Test 1B and 2C and Reference product (2 tablets of Aulin® 100 mg) of Nimesulide from Example 24.

Result:
FIG. 10 depicts a graphical comparison of the dose normalized plasma concentration time profiles of the Test and Reference products.
Pharmacokinetic Parameters (Statistical Analysis):

TABLE 14

Summary of statistical comparisons of dose-normalized nimesulide results for Test-1B, Test 2C and Reference.

| | Least-Squares Means[1] | | | | | |
|---|---|---|---|---|---|---|
| Parameter | Test-1 | Reference | Ratio[2] | Test-2 | Reference | Ratio[2] |
| Tmax (hour) | 9.67 | 2.83 | 3.412* | 8.56 | 2.83 | 3.022* |
| Ke (1/hour) | 0.1863 | 0.1959 | 0.951 | 0.2039 | 0.1959 | 1.041 |
| T½ (hour) | 3.97 | 4.10 | 0.967 | 5.30 | 4.10 | 1.291 |
| | Ln-Transformed: | | | | | |
| AUC 0-t (ng-hr/ml) | 120 | 130 | 0.917 | 109 | 130 | 0.839 |
| AUCinf (ng-hr/ml) | 127 | 134 | 0.947 | 128 | 134 | 0.953 |
| Cmax (ng/ml) | 12.5 | 17.2 | 0.726* | 12.4 | 17.2 | 0.717* |

[1]Least-squares geometric means for ln-transformed data.
[2]Ratio calculated as Test least-squares mean divided by the Reference least-squares mean.
*Comparison was detected as statistically significant by ANOVA ($\alpha = 0.05$).

Summary: The Tmax of the Test formulation increased (8-10 hours) as compared to the immediate release formulation of Nimesulide with Tmax of 2-3 hours. The Cmax of Test products decreased as compared to the Reference product. The AUC of Test and Reference products were found to be comparable.

The invention claimed is:

1. A buoyant system for spatially and temporally programmable delivery of an active agent comprising a solid core, one or more layers coated over the core and a preformed hollow space; wherein the active agent is present in the core or any of the layers of the system and wherein the preformed hollow space is present between two or more layers or between the core and one or more layers of the system or both.

2. The system of claim 1 comprising a core, a polymeric layer, an active agent containing layer coated over the polymeric layer and a preformed hollow space.

3. The system of claim 2 comprising an additional polymeric layer coated over the core.

4. The system of claim 2 wherein an active agent is also present in the core and wherein the active agent is same or different from that present in the active agent containing layer.

5. The system of claim 2 comprising
   a core optionally comprising an active agent;
   a first polymeric layer comprising a hydrophilic material;
   a second polymeric layer comprising a polymer substantially insoluble in the gastric fluid;
   an active agent containing layer coated over the second polymeric layer;
   and a preformed hollow space substantially present between the first polymeric layer and the second polymeric layer.

6. The system of claim 5 further comprising an additional layer coated on the active agent containing layer, the core or the second polymeric layer, wherein the additional layer comprises of a hydrophilic material.

7. The system of claim 5 wherein the core comprises of about 10% to about 99.5% w/w diluent, about 0% to about 50% w/w binder and about 0.05% to about 10% w/w of lubricant.

8. The system of claim 5 wherein the core comprises of an active agent and an absorption enhancer, wherein the absorption enhancer is selected from the group of cell envelope disordering compounds, solvents, steroidal detergents, chelators; surfactants; bile salts; fatty; non-surfactants and combinations thereof.

9. The system of claim 5 wherein the hydrophilic material of the first polymeric layer is selected from the group of celluloses, alkylcelluloses, alkali metal salts of carboxyalkylcelluloses, polysaccharides, polyacrylic acids and their salts, polymethacrylic acids and their salts, methacrylate copolymers, vinyl polymers and copolymers, polymers and copolymers of polyalkylene oxides and hygroscopic or deliquescent materials.

10. The system of claim 5 wherein the polymer of the second polymeric layer is selected from the group of enteric cellulose derivatives, enteric acrylic acid-based polymers and copolymers, enteric maleic acid-based polymers and copolymers, enteric polyvinyl derivatives, zein, shellac, cellulose esters, ethylcellulose, cellulose acetate, and enzymatically degradable polymers.

11. The system of claim 5 wherein the polymer of the second polymeric layer is selected from the group of acrylic and methacrylic acid based polymers and copolymers, ethylcellulose, cellulose acetate, hydroxypropyl methyl cellulose phthalate and cellulose acetate phthalate.

12. The system of claim 5 wherein the second polymeric layer comprises of a plasticizer upto about 50% w/w of the dry weight of the polymer.

13. The system of claim 5 wherein the second polymeric layer comprises of about 10% to about 100% w/w polymer, about 0% to about 40% w/w plasticizer and about 0% to about 50% w/w anti-tacking agent and wherein the polymer is coated in the range from about 5% to about 50% w/w of the system.

14. The system of claim 5 wherein the active agent containing layer also comprises a matrix or coating of a rate controlling material selected from the group of natural and synthetic polymers, gums of plant, animal, mineral or synthetic origin, substituted or unsubstituted hydrocarbons, fatty acids, fatty alcohols, glyceryl esters of fatty acids, minerals, vegetable oils and waxes.

15. The system of claim 14, wherein the rate controlling material is selected from the group of hydroxypropyl methyl cellulose, polyvinyl pyrrolidone, ethyl cellulose, and poly (methacrylate) co-polymers.

16. The system of claim 5 wherein the active agent containing layer comprises of a mucoadhesive substance.

17. The system of claim 1 wherein the active agent is selected from the group of active agents used for alzheimer's disease, antibiotics, antiulcers, anti-muscarinic agents, antivirals, anaesthetics, acromegaly agents, steroidal and non-steroidal anti-inflammatory agents, analgesics, antiasthmatics, anticancer agents, anticoagulants and antithrombotic agents, anticonvulsants, antidiabetics, antiemetics, alcohol abuse preparations, antiglaucoma, antiallergics, antihistamines, anti-infective agents, antiparkinsons, antiplatelet agents, antirheumatic agents, anti spasmodics and anticholinergic agents, antitussives, carbonic anhydrase inhibitors, cardiovascular agents, cholinesterase inhibitors, treatment of CNS disorders, CNS stimulants, contraceptives, cystic fibrosis management, dopamine receptor agonists, endometriosis management, erectile dysfunction therapy, urinary tract disinfectants, fertility agents, gastrointestinal agents, immunomodulators and immunosuppressives, vitamins, nutritives, memory enhancers, migraine preparations, muscle relaxants, nucleoside analogues, osteoporosis management, active agents for respiratory organs, parasympathomimetics, prostaglandins, P-gp inhibitors, psychotherapeutic agents, sedatives, hypnotics and tranquillizers, agents used for early morning pathologies, macromolecules and combinations thereof.

18. The system of claim 1 wherein the active agent is selected from the group of nimesulide, carvedilol, fenofibrate, tacrolimus, baclofen, metformin, loratidine, pseudoephedrine sulfate, bicalutamide, tramadol and leuprolide enalapril, captopril, benazepril, lisinopril, ranitidine, famotidine, diltiazem, propranolol, verapamil, nifedipine, acyclovir, ciprofloxacin, simvastatin, atorvastatin, dasatinib, pravastatin, lovastatin, selegiline, midazolam, glimepiride, glipizide and nefazodone.

19. The system of claim 1, wherein the active agent is selected from the class of active agents having enhanced solubility in the gastric pH.

20. The system of claim 1, wherein the system is an immediate release or a modified release system and wherein the system is administered orally and is retained in the gastric region for a period of time from about 1 hour to about 18 hours.

21. The system of claim 4 wherein the active agent present in the active agent containing layer is delivered in the gastric and/or the upper intestinal region and the active agent present in the core is delivered in the lower intestinal and/or the colonic region, when the system is administered orally.

22. The system of claim 21 wherein the system exhibits pulsatile release, one pulse released on administration and the other pulse is released after a predetermined delay and wherein one or both the pulses are modified release pulses.

23. The system of claim 1 comprising a core, one or more polymeric layers coated over the core and a preformed hollow space, wherein the active agent is present in the core and wherein the active agent is delivered as an immediate or modified release in the lower intestinal and/or the colonic region when the system is administered orally.

24. The system of claim 1 comprising a core comprising an active agent, one or more layers coated over the core and a preformed hollow space; wherein the core comprises of a rate controlling material in a matrix or coating form.

25. The system of claim 1 comprising
a core comprising a hydrophilic material;
a polymeric layer comprising a polymer substantially insoluble in the gastric fluid;
an active agent containing layer;
and a preformed hollow space wherein the preformed hollow space is present substantially between the core and the polymeric layer.

26. The system of claim 1, wherein the system is in the form of a tablet, capsule, bead or a pellet.

27. The system of claim 1 in the form of a tablet, wherein the tablet is round, oval, capsule shaped, spherical, cylindrical, triangular, square, rectangular or polygonal in shape.

28. The system of claim 2 comprising
a core optionally comprising an active agent;
a first polymeric layer comprising a hydrophobic material;
a second polymeric layer comprising a polymer substantially insoluble in the gastric fluid;
an active agent containing layer coated over the second polymeric layer;
and a preformed hollow space substantially present between the first polymeric layer and the second polymeric layer.

29. A process for manufacturing a buoyant system for spatially and temporally programmable delivery of an active agent, the system comprising a core, one or more layers coated over the core and a preformed hollow space, the process comprising the steps of:
i. manufacturing a core or using a preformed core, optionally with an active agent;
ii. optionally coating the core with a hydrophilic material to form the first polymeric layer;
iii. further coating the system with a polymer substantially insoluble in the gastric fluid to form the second polymeric layer;
iv. supplying energy and/or vacuum over a period ranging from about a few seconds to about 5 hours, causing the expansion of the second polymeric layer and generation of a hollow space; and
v. optionally coating the system manufactured in step iv) with an active agent to form an active agent containing layer.

30. The process of claim 29, comprising the steps of:
i. manufacturing a core in the form of a tablet, optionally with an active agent;
ii. coating the core with a hydrophilic material to form the first polymeric layer;
iii. coating the system manufactured in step ii) with a polymer substantially insoluble in the gastric fluid to form the second polymeric layer;
iv. supplying heat in the range of about 40° C. to about 150° C. after step iii), causing the expansion of the second polymeric layer and subsequent cooling leading to generation of a hollow space; and
v. coating the system manufactured in step iv) with an active agent to form an active agent containing layer.

31. The process of claim 29, further comprising the step of coating an additional layer on the active agent containing layer, the core or over the second polymeric layer, wherein the additional layer comprises of a hydrophilic material.

32. The process of claim 29, wherein the hollow space comprises air, vapor, a gas, a mixture of gases or a partial vacuum.

33. The process of claim 29, wherein the active agent containing layer is coated as a solution or dispersion of an active agent and an excipient.

34. The process of claim 29, wherein the active agent containing layer is manufactured by coating a layer of an active agent followed by coating a layer of a rate controlling material.

35. A buoyant system retained in the gastric region for a prolonged period of time comprising a solid core, one or more layers coated over the core and a preformed hollow space; wherein the active agent is present in the core or any of the layers of the system and wherein the preformed hollow space is substantially present between two or more layers or between the core and one or more layers of the system or both.

36. A process for manufacturing a buoyant system having a density lesser than gastric fluid comprising the step of formation of a hollow space within the system due to expansion of one or more of its compartments, the expansion being caused by generation of a positive or negative pressure within the system.

37. The process of claim 36, wherein the positive pressure is vapor pressure generated due to supply of energy and wherein the negative pressure is generated due to a supply of vacuum.

38. The process of claim 36, wherein the expansion is caused by a combined supply of energy and vacuum.

39. The process of claim 37, wherein the energy is heat, which is supplied in the range of about 40° C. to about 150° C.

40. The process of claim 37, wherein the energy is supplied over a period ranging from about a few seconds to about 5 hours.

41. A system manufactured by the process of claim 36, wherein the system comprises of a core, one or more layers coated over the core and the preformed hollow space.

42. The system of claim 9 wherein the hydrophilic material of the first polymeric layer is selected from the group of polyvinyl alcohol, polyvinylpyrrolidone, vinylpyrrolidone-vinyl acetate copolymer and hydroxyalkylcelluloses in the range of from about 10% to about 100% w/w of the layer.

43. The system of claim 5 wherein the hydrophilic material is coated in the range from about 2% to about 50% w/w of the system.

44. The system of claim 1, wherein the active agent is selected from the class of active agents preferentially absorbed through the proximal region of the gastrointestinal tract.

45. The system of claim 1, wherein the active agent is selected from the class of active agents, which act locally in the proximal region of the gastrointestinal tract.

46. The system of claim 1, wherein the active agent is selected from the class of active agents degraded due to intestinal pH and/or enzymes.

47. The system of claim 1, wherein the active agent is present in an amount ranging from about 0.5% to about 85% w/w of the system.

* * * * *